United States Patent
Askari et al.

(10) Patent No.: US 10,189,773 B2
(45) Date of Patent: Jan. 29, 2019

(54) IN-VIVO GELLING PHARMACEUTICAL PRE-FORMULATION

(75) Inventors: Syed H. Askari, San Jose, CA (US); George Horng, Millbrae, CA (US)

(73) Assignee: MEDICUS BIOSCIENCES, LLC, San Francisco, CA (US)

( * ) Notice: Subject to any disclaimer, the term of this patent is extended or adjusted under 35 U.S.C. 154(b) by 0 days.

(21) Appl. No.: 13/696,032

(22) PCT Filed: May 6, 2011

(86) PCT No.: PCT/US2011/035643
§ 371 (c)(1),
(2), (4) Date: Jan. 15, 2013

(87) PCT Pub. No.: WO2011/140519
PCT Pub. Date: Nov. 10, 2011

(65) Prior Publication Data
US 2013/0116341 A1    May 9, 2013

Related U.S. Application Data

(60) Provisional application No. 61/387,841, filed on Sep. 29, 2010, provisional application No. 61/378,730, filed on Aug. 31, 2010, provisional application No. 61/332,197, filed on May 7, 2010.

(51) Int. Cl.
| | | |
|---|---|---|
| *C07C 229/24* | (2006.01) |
| *A61K 9/00* | (2006.01) |
| *A61K 49/04* | (2006.01) |
| *A61K 47/34* | (2017.01) |
| *C08G 65/34* | (2006.01) |

(52) U.S. Cl.
CPC .......... *C07C 229/24* (2013.01); *A61K 9/0002* (2013.01); *A61K 9/0078* (2013.01); *A61K 47/34* (2013.01); *A61K 49/04* (2013.01); *C08G 65/34* (2013.01)

(58) Field of Classification Search
None
See application file for complete search history.

(56) References Cited

U.S. PATENT DOCUMENTS

| | | |
|---|---|---|
| 5,037,384 A | 8/1991 | Chang |
| 5,135,755 A | 8/1992 | Czech et al. |
| 5,336,175 A | 8/1994 | Mames |
| 5,858,345 A | 1/1999 | Charles et al. |
| 5,874,500 A | 2/1999 | Rhee et al. |
| 6,051,648 A | 4/2000 | Rhee et al. |
| 6,135,118 A | 10/2000 | Dailey |
| 6,149,931 A | 11/2000 | Schwartz et al. |
| 6,153,211 A | 11/2000 | Hubbell et al. |
| 6,180,687 B1 | 1/2001 | Hammer et al. |
| 6,207,772 B1 | 3/2001 | Hatsuda et al. |
| 6,312,725 B1 | 11/2001 | Wallace et al. |
| 6,458,889 B1 * | 10/2002 | Trollsas et al. .............. 525/54.1 |
| 6,475,508 B1 | 11/2002 | Schwartz et al. |
| 6,547,714 B1 | 4/2003 | Dailey |
| 6,566,406 B1 | 5/2003 | Pathak et al. |
| 6,605,294 B2 | 8/2003 | Sawhney |
| 6,624,245 B2 | 9/2003 | Wallace et al. |
| 6,632,457 B1 | 10/2003 | Sawhney |
| 6,703,037 B1 | 3/2004 | Hubbell et al. |
| 6,703,378 B1 | 3/2004 | Kunzler et al. |
| 6,818,018 B1 | 11/2004 | Sawhney |
| 7,009,343 B2 | 3/2006 | Lim et al. |
| 7,255,874 B1 | 8/2007 | Bobo et al. |
| 7,332,566 B2 | 2/2008 | Pathak et al. |
| 7,553,810 B2 | 6/2009 | Gong et al. |
| 7,592,418 B2 | 9/2009 | Pathak et al. |
| 8,388,995 B1 | 3/2013 | All et al. |
| 8,765,787 B2 | 7/2014 | Aberg et al. |
| 8,987,339 B2 | 3/2015 | Askari et al. |
| 9,072,809 B2 | 7/2015 | Askari et al. |
| 9,149,560 B2 | 10/2015 | Askari et al. |
| 2001/0003126 A1 | 6/2001 | Rhee et al. |
| 2001/0055615 A1 | 12/2001 | Wallace et al. |
| 2002/0042473 A1 | 4/2002 | Trollsas et al. |
| 2002/0106409 A1 | 8/2002 | Sawhney |
| 2002/0114775 A1 | 8/2002 | Pathak |
| 2002/0165337 A1 | 11/2002 | Wallace et al. |
| 2003/0195113 A1 | 10/2003 | Nakamura et al. |
| 2003/0223957 A1 | 12/2003 | Schwartz et al. |

(Continued)

FOREIGN PATENT DOCUMENTS

| | | |
|---|---|---|
| CA | 2750242 A1 | 8/2010 |
| JP | 2011-505420 A | 2/2011 |

(Continued)

OTHER PUBLICATIONS

JenKem Technology USA, "Multi-arm PEG Derivatives," 2013, http://www.jenkemusa.com/Pages/MultiarmPEGs.aspx.*
3M Company, 3M™ Vetbond™ Veterinary Tissue Adhesive, Material Safety Data Sheet, Jun. 1, 2009.
Abbott Animal Health, GLUture®, Information Brochure, Feb. 2009.
Baino, "Towards an ideal biomaterial for vitreous replacement: Historical overview and future trends," Acta Biomaterialia 7: 921-935 (2011).
Brandi et al., "Biodegradable hydrogels for time-controlled release of tethered peptides or proteins," Biomacromolecules 11: 496-504 (2010).
Campbell et al., "Evaluation of the PleuraSeal™ Lung Sealant System as a Thoracic Sealant in a Canine Lung Resection Model," Covidien (2007).

(Continued)

*Primary Examiner* — Craig D Ricci
(74) *Attorney, Agent, or Firm* — Pepper Hamilton LLP

(57) ABSTRACT

Provided herein are in vivo gelling pharmaceutical pre-formulations forming biocompatible hydrogel polymers that are polymerized in vivo and kits comprising at least one nucleophilic compound or monomer unit, at least one electrophilic compound or monomer unit, and optionally at least one therapeutic agent. The biocompatible hydrogel polymer is bioabsorbable and releases the therapeutic agent at a target site, avoiding systemic exposure.

14 Claims, 2 Drawing Sheets

(56) References Cited

U.S. PATENT DOCUMENTS

| | | |
|---|---|---|
| 2004/0009205 A1 | 1/2004 | Sawhney |
| 2004/0018228 A1 | 1/2004 | Fischell et al. |
| 2004/0023842 A1 | 2/2004 | Pathak et al. |
| 2004/0033264 A1 | 2/2004 | Sawhney |
| 2004/0203149 A1 | 10/2004 | Childs et al. |
| 2005/0027069 A1 | 2/2005 | Rhee et al. |
| 2005/0191277 A1 | 9/2005 | Fisher |
| 2005/0200295 A1 | 9/2005 | Lim et al. |
| 2005/0203333 A1 | 9/2005 | Dailey |
| 2005/0208102 A1 | 9/2005 | Schultz |
| 2005/0255039 A1 | 11/2005 | Desai |
| 2005/0281802 A1 | 12/2005 | Gong et al. |
| 2005/0281883 A1 | 12/2005 | Daniloff et al. |
| 2006/0057208 A1 | 3/2006 | Holzer et al. |
| 2006/0065199 A1 | 3/2006 | Davis |
| 2006/0115457 A1 | 6/2006 | Hnojewyj |
| 2006/0147409 A1 | 7/2006 | Pathak et al. |
| 2006/0159771 A1 | 7/2006 | Kadrmas |
| 2006/0222596 A1 | 10/2006 | Askari et al. |
| 2007/0110813 A1 | 5/2007 | Ingenito et al. |
| 2008/0095736 A1 | 4/2008 | Pathak et al. |
| 2008/0115787 A1 | 5/2008 | Ingenito |
| 2008/0159975 A1 | 7/2008 | Nho et al. |
| 2008/0160085 A1 | 7/2008 | Boland et al. |
| 2008/0214695 A1 | 9/2008 | Pathak et al. |
| 2008/0261884 A1* | 10/2008 | Tsai et al. ........ 514/12 |
| 2008/0279944 A1 | 11/2008 | Sawhney |
| 2008/0281352 A1 | 11/2008 | Ingenito et al. |
| 2009/0087443 A1 | 4/2009 | Bartels |
| 2009/0170811 A1 | 7/2009 | Garvey et al. |
| 2009/0196928 A1* | 8/2009 | Hnojewyi ........ 424/486 |
| 2009/0215923 A1 | 8/2009 | Carnahan et al. |
| 2010/0040538 A1 | 2/2010 | Ingenito et al. |
| 2010/0055078 A1 | 3/2010 | Hughes-Fulford |
| 2010/0113476 A1 | 5/2010 | Chen et al. |
| 2011/0081701 A1 | 4/2011 | Sargeant et al. |
| 2011/0091551 A1 | 4/2011 | Baur et al. |
| 2012/0295869 A1 | 11/2012 | Liu et al. |
| 2013/0108711 A1 | 5/2013 | Askari et al. |
| 2013/0116341 A1 | 5/2013 | Askari et al. |
| 2014/0248231 A1 | 9/2014 | Askari et al. |
| 2014/0271528 A1 | 9/2014 | Askari et al. |
| 2014/0271767 A1 | 9/2014 | Askari et al. |
| 2014/0302051 A1 | 10/2014 | Askari et al. |
| 2015/0190544 A1 | 7/2015 | Askari et al. |
| 2015/0272987 A1 | 10/2015 | Askari et al. |
| 2015/0273108 A1 | 10/2015 | Askari et al. |

FOREIGN PATENT DOCUMENTS

| | | | |
|---|---|---|---|
| JP | 2011-505420 A | 2/2011 | |
| JP | 201281252 A | 4/2012 | |
| WO | WO-1997-22371 | 6/1997 | |
| WO | WO-1999-003454 | 1/1999 | |
| WO | WO-2001-010416 | 2/2001 | |
| WO | WO 02053526 A1 * | 7/2002 | |
| WO | 2002/062276 A1 | 8/2002 | |
| WO | WO 2002/102864 * | 12/2002 | ........... C08F 283/00 |
| WO | WO-02102864 A1 | 12/2002 | |
| WO | WO-2004-021983 | 3/2004 | |
| WO | WO-2006-030431 | 3/2006 | |
| WO | WO-2007016622 A2 | 2/2007 | |
| WO | WO-2008-141059 | 11/2008 | |
| WO | 2009/073192 A2 | 6/2009 | |
| WO | WO-2009-123768 | 10/2009 | |
| WO | WO-2009-132153 | 10/2009 | |
| WO | WO-2010064251 A1 | 6/2010 | |
| WO | 2010076400 A8 | 9/2010 | |
| WO | WO-2011-057131 | 5/2011 | |
| WO | 2011066291 A2 | 6/2011 | |
| WO | WO-2011-066291 | 6/2011 | |
| WO | 2011140519 A2 | 11/2011 | |
| WO | WO-2011-140517 | 11/2011 | |
| WO | WO-2011-140519 | 11/2011 | |
| WO | 2012050591 A1 | 4/2012 | |
| WO | WO-2012057628 A2 | 5/2012 | |

OTHER PUBLICATIONS

Creative PEGWorks, Multiarm PEG materials, PEG product Catalog, last updated Dec. 31, 2012.

Dango et al., "Initial experience with a synthetic sealant PleuraSeal™ after pulmonary resections: a prospective study with retrospective case matched controls," Journal of Cardiothoracic Surgery 5: 50-58 (2010).

Ethicon, Inc., Ethicon™ Dermabond Advanced™, Instructions for Use, Status Mar. 2011.

Jemyork Biotechnology, Multiarm PEG materials, web pages printed from www.jemyork.com/proshow.aspx?id=131 on Feb. 12, 2013.

JenKem Technology, USA, Multiarm PEG materials, PEG Products Catalog, 2011.

NanoCS, Inc., Multiarm PEG Derivatives, web pages printed from http://www.nanocs.com/PEG/MAPEG.htm on Feb. 12, 2013.

NeoMend, Inc., ProGEL®, Instructions for Use and Product Labeling, Jan. 4, 2012.

NOF Corporation, Drug Delivery Systems, Catalogue Ver. 13, Prepared Oct. 2011.

Preul et al., "Application of a new hydrogel dural sealant that reduces epidural adhesion formation: evaluation in a large animal laminectomy model," J Neurosurg Spine 12: 381-390 (2010).

International Search Report and Written Opinion for PCT/US2011/035640, dated Jan. 19, 2012.

International Search Report and Written Opinion for PCT/US2011/035643, dated Jan. 19, 2012.

International Search Report for PCT/US2013/040619 dated Sep. 27, 2013.

Lazzarin et al., N. Engl. J. Med., 348(22):2186-2195 (2003).

Marcus et al., J. Bone Miner. Res. 18:18-23 (2003).

Neer et al., New Engl. J. Med., 344:1434-1441 (2001).

U.S. Appl. No. 13/696,028 Office Action dated Dec. 31, 2013.

PCT/US2014/028798 International Search Report dated Aug. 26, 2014.

U.S. Appl. No. 13/696,028 Office Action dated Nov. 7, 2014.

U.S. Appl. No. 14/273,408 Office Action dated Aug. 29, 2014.

U.S. Appl. No. 14/273,408 Office Action dated Nov. 18, 2014.

Co-pending US patent application No. US201514618804, filed on Feb. 10, 2015.

U.S. Appl. No. 13/571,116 Office Action dated Mar. 4, 2015.

Sardari et al. Evaluation of Clinical Examination for Differential Diagnosis of Lameness by Navicular Apparatus or Heel Pain in Horses. Pakistan Journal of Biological Sciences 11(13):1754-1756 (2008).

U.S. Appl. No. 14/722,829 Office Action dated Aug. 18, 2015.

U.S. Appl. No. 14/739,917 Office Action dated Aug. 4, 2015.

Co-pending U.S. Appl. No. 14/722,829, filed May 27, 2015.

Co-pending U.S. Appl. No. 14/739,917, filed Jun. 15, 2015.

U.S. Appl. No. 13/696,028 Office Action dated Jul. 17, 2015.

Bailico et al. MultiPEGs: High Molecular Weight Multifunctional Poly(ethylene glycol)s Assembled by a Denrimer-Like Approach. Eur. J. Org. Chem. pp. 2064-2073, (2005).

Co-pending U.S. Appl. No. 14/947,818, filed Nov. 20, 2015.

U.S. Appl. No. 13/571,116 Office Action dated Oct. 22, 2015.

U.S. Appl. No. 13/571,116 Office Action dated Nov. 10, 2016.

Ostroha. PEG-based Degradable Networks for Drug Delivery Applications. Thesis (165 pgs.) (Jun. 2006).

U.S. Appl. No. 14/739,917 Office Action dated Nov. 25, 2016.

U.S. Appl. No. 14/947,818 Office Action dated Nov. 23, 2016.

Goudar. Review of pemetrexed in combination with cisplatin for the treatment of malignant pleural mesothelioma. Ther Clin Risk Manag 4(1):205-211 (2008).

U.S. Appl. No. 13/571,116 Office Action dated Apr. 27, 2016.

U.S. Appl. No. 13/696,028 Office Action dated Sep. 2, 2016.

U.S. Appl. No. 14/722,829 Office Action dated Aug. 24, 2016.

U.S. Appl. No. 14/722,829 Office Action dated Feb. 5, 2016.

U.S. Appl. No. 14/739,917 Office Action dated Jan. 22, 2016.

(56) References Cited

OTHER PUBLICATIONS

U.S. Appl. No. 14/739,917 Office Action dated May 11, 2016.
U.S. Appl. No. 14/947,818 Office Action dated May 9, 2016.
U.S. Appl. No. 14/947,818 Office Action dated Apr. 16, 2018.
U.S. Appl. No. 15/467,019, Nonfinal Office Action dated Mar. 8, 2018.
EP1317998.3 Search Report dated Feb. 13, 2014.
Nicodemus et al., Cell encapsulation in biodegradable hydrogels for tissue engineering applications, Tissue Engineering Part B 2008 14(2):149-165.
U.S. Appl. No. 13/696,032 Office Action dated Dec. 10, 2014.
U.S. Appl. No. 13/696,032 Office Action dated Jan. 6, 2017.
U.S. Appl. No. 13/696,032 Office Action dated Jul. 17, 2015.
U.S. Appl. No. 13/696,032 Office Action dated Jun. 12, 2014.
U.S. Appl. No. 13/696,032 Office Action dated Jun. 8, 2016.
U.S. Appl. No. 13/696,032 Office Action dated Oct. 22, 2013.
U.S. Appl. No. 14/213,520 Office Action dated Dec. 15, 2014.
U.S. Appl. No. 14/273,408 Notice of Allowance dated Feb. 10, 2017.
U.S. Appl. No. 14/739,917 Office Action dated Jun. 13, 2017.
U.S. Appl. No. 14/722,829 Notice of Allowance dated Feb. 10, 2017.
PCT/US2014/028622 International Search Report dated Jul. 7, 2014.
U.S. Appl. No. 14/212,457 Office Action dated Jun. 9, 2014.
U.S. Appl. No. 13/696,028 Office Action dated Jun. 12, 2014.
U.S. Appl. No. 14/213,520 Office Action dated Jul. 3, 2014.

* cited by examiner

IN-VIVO GELLING PHARMACEUTICAL PRE-FORMULATION

CROSS-REFERENCE

This application is filed pursuant to 35 U.S.C. § 371 as a United States National Phase Application of International Application Ser. No. PCT/US11/035643, filed May 6, 2011, which claims the benefit of U.S. Provisional Application No. 61/387,841, filed Sep. 29, 2010, U.S. Provisional Application No. 61/378,730, filed Aug. 31, 2010, and U.S. Provisional Application No. 61/332,197, filed May 7, 2010, each of which are incorporated herein by reference in their entirety.

BACKGROUND OF THE INVENTION

Every year millions of people undergo systemic treatments, such as chemotherapy for cancers, inflammatory diseases, and chronic conditions. Systemic treatments, in which medications are injected or absorbed into the bloodstream an circulated throughout the body, are currently the only viable option to reach the site of these diseases even though in most cases the disease is localized in a specific organ. However, the systemic approach produces toxic side effects, such as profound nausea and vomiting, immunosuppression and risk or life threatening infections, anemia, hair loss, kidney toxicity, and nerve damage. For many cancer patients the toxicity potential is so severe that chemotherapy cannot be given. In some instances, patients die of the side effects rather than from the cancer.

SUMMARY OF THE INVENTION

Provided herein are in vivo gelling pharmaceutical pre-formulations, biocompatible hydrogel polymers, in vivo polymerized biocompatible hydrogel polymers, and kits for preparing in vivo gelling pharmaceutical pre-formulations, biocompatible hydrogel polymers, and in vivo polymerized biocompatible hydrogel polymers. The pre-formulations and hydrogel polymers comprise a mixture of compounds that safely undergo polymerization to form a biocompatible hydrogel polymer at a target site. Using a minimally invasive delivery system (e.g., endoscopic or image guided), the polymeric hydrogel formulation is delivered to the target site, where the pre-formulation solidifies into a biocompatible hydrogel polymer at a predetermined time to remain at the site of delivery. In some embodiments, the biocompatible hydrogel polymer comprises one or more therapeutic agents that are released over time from the hydrogel polymer at the target site, limiting exposure of healthy cells to the therapeutic agent. In certain embodiments, the biocompatible hydrogel polymer degrades over time and is bioabsorbed.

In one aspect provided herein is an in vivo gelling pharmaceutical pre-formulation, comprising (a) at least one water soluble first compound comprising more than one nucleophilic group, (b) at least one water soluble second compound comprising more than one electrophilic group, (c) an aqueous buffer in the pH range of 5.0 to 9.0; and (d) optionally, one or more therapeutic agents; wherein mixing the first compound, the second compound, and the optional therapeutic agent in the aqueous buffer and delivering the mixture to a target site in the human body generates the in vivo gelling pharmaceutical pre-formulation such that the in vivo gelling pharmaceutical pre-formulation at least in part polymerizes and gels at the target site to form a biocompatible hydrogel polymer.

In some embodiments, the nucleophilic group is a thiol or amino group. In certain embodiments, the first compound is a glycol, trimethylolpropane, pentaerythritol, hexaglycerol, or tripentaerythritol derivative. In preferred embodiments, the first compound is a pentaerythritol or hexaglycerol derivative. In certain embodiments, the first compound further comprises one or more polyethylene glycol sections. In some embodiments, the first compound is selected from the group consisting of ethoxylated pentaerythritol ethylamine ether, ethoxylated pentaerythritol propylamine ether, ethoxylated pentaerythritol amino acetate, ethoxylated hexaglycerol ethylamine ether, ethoxylated hexaglycerol propylamine ether, and ethoxylated hexaglycerol amino acetate. In certain embodiments, the first compound is selected from the group consisting of trimethylolpropane trimercaptoacetate, trimethylolpropane tri-3-mercaptopropionate, pentaerythritol tetramercaptoacetate, pentaerythritol tetra-3-mercaptopropionate, ethoxylated trimethylolpropane trimercaptoacetate, ethoxylated trimethylolpropane tri-3-mercaptopropionate, ethoxylated pentaerythritol tetramercaptoacetate, and ethoxylated trimethylolpropane tri-3-mercaptopropionate. In some embodiments, the molecular weight of the first compound is between about 1000 and 20000.

In certain embodiments, the electrophilic group is an epoxide, N-succinimidyl succinate, N-succinimidyl glutarate, N-succinimidyl succinamide or N-succinimidyl glutaramide. In some embodiments, the second compound is a trimethylolpropane, glycerol, diglycerol, pentaerythritol, sorbitol, hexaglycerol, tripentaerythritol, or polyglycerol derivative. In preferred embodiments, the second compound is a trimethylolpropane, pentaerythritol, or hexaglycerol derivative. In some embodiments, the second compound further comprises one or more polyethylene glycol sections. In certain embodiments, the second compound is selected from the group consisting of ethoxylated pentaerythritol succinimidyl succinate, ethoxylated pentaerythritol succinimidyl glutarate, ethoxylated pentaerythritol succinimidyl glutaramide, ethoxylated hexaglycerol succinimidyl succinate, ethoxylated hexaglycerol succinimidyl glutarate, and ethoxylated hexaglycerol succinimidyl glutaramide. In some embodiments, the second compound is selected from the group consisting of sorbitol polyglycidyl ether, polyglycerol polyglycidyl ether, diglycerol polyglycidyl ether, glycerol polyglycidyl ether, and trimethylolpropane polyglycidyl ether. In certain embodiments, the molecular weight of the second compound is between about 1000 and 20000.

In some embodiments, the therapeutic agent is independently selected from the group consisting of an anticancer agent, an antiviral agent, an antibacterial agent, antifungal agent, an immunosuppressant agent, an hemostasis agent, and an anti-inflammatory agent.

In certain embodiments, the gelling time of the biocompatible hydrogel polymer is controlled by the pH of the aqueous buffer. In some embodiments, the gelling time is between about 20 seconds and 5 minutes. In certain embodiments, the pH of the aqueous buffer is from about 6.9 to about 7.9. In some embodiments, the pH of the aqueous buffer is about 7.4. In certain embodiments, the biocompatible hydrogel polymer gels at a predetermined time. In some embodiments, the biocompatible hydrogel polymer is a bioabsorbable polymer. In certain embodiments, the biocompatible hydrogel polymer is bioabsorbed within about 1 to 70 days. In some embodiments, the biocompatible hydrogel polymer is substantially non-bioabsorbable. In certain embodiments, the in vivo gelling pharmaceutical pre-formulation further comprises a radiopaque material or a pharmaceutically acceptable dye. In certain embodiments, the radiopaque material is selected from sodium iodide, potassium iodide, barium sulfate, tantalum, VISIPAQUE®, OMNIPAQUE®, or HYPAQUE®, or combinations thereof.

In some embodiments, the therapeutic agent is released from the biocompatible hydrogel polymer through diffusion, osmosis, degradation of the biocompatible hydrogel polymer, or any combination thereof. In certain embodiments, the therapeutic agent is initially released from the biocompatible hydrogel polymer through diffusion and later released through degradation of the biocompatible hydrogel polymer. In some embodiments, the therapeutic agent is substantially released from the biocompatible hydrogel polymer within 180 days. In certain embodiments, the therapeutic agent is substantially released from the biocompatible hydrogel polymer within 14 days. In some embodiments, the therapeutic agent is substantially released from the biocompatible hydrogel polymer within 24 hours. In certain embodiments, the therapeutic agent is substantially released from the biocompatible hydrogel polymer within one hour. In some embodiments, the first compound and the second compound do not react with the therapeutic agent during formation of the biocompatible hydrogel polymer. In certain embodiments, the biocompatible hydrogel polymer interacts with the therapeutic agent, and wherein more than 10% of the therapeutic agent is released through degradation of the biocompatible hydrogel polymer. In some embodiments, more than 30% of the therapeutic agent is released through degradation of the biocompatible hydrogel polymer. In certain embodiments, the biocompatible hydrogel polymer interacts with the therapeutic agent by forming covalent bonds between the biocompatible hydrogel polymer and the therapeutic agent. In some embodiments, the biocompatible hydrogel polymer interacts with the therapeutic agent by forming a non-covalent bond between the biocompatible hydrogel polymer and the therapeutic agent.

In another aspect provided herein is a biocompatible hydrogel polymer made by mixing (a) at least one water soluble first compound comprising more than one nucleophilic group, (b) at least one water soluble second compound comprising more than one electrophilic group, (c) an aqueous buffer in the pH range of 5.0 to 9.0, and (d) optionally, one or more therapeutic agents. In some embodiments, the mixing is performed outside a human body, and the biocompatible hydrogel polymer gels inside the human body. In certain embodiments, the mixing is performed outside the human body, and the biocompatible hydrogel polymer gels at least in part inside the human body. In some embodiments, the mixing is performed during delivery to a target site inside a human body, and the biocompatible hydrogel polymer gels at least in part inside the human body.

In certain embodiments, the nucleophilic group is a thiol or amino group. In some embodiments, the first compound is a glycol, trimethylolpropane, pentaerythritol, hexaglycerol, or tripentaerythritol derivative. In certain embodiments, the first compound further comprises one or more polyethylene glycol sections. In some embodiments, the first compound is selected from the group consisting of ethoxylated pentaerythritol ethylamine ether, ethoxylated pentaerythritol propylamine ether, ethoxylated pentaerythritol amino acetate, ethoxylated hexaglycerol ethylamine ether, ethoxylated hexaglycerol propylamine ether, ethoxylated trimethylolpropane tri-3-mercaptopropionate, ethoxylated hexaglycerol amino acetate.

In some embodiments, the electrophilic group is an epoxide, N-succinimidyl succinate, N-succinimidyl glutarate, N-succinimidyl succinamide, or N-succinimidyl glutaramide. In certain embodiments, the second compound is a trimethylolpropane, glycerol, diglycerol, pentaerythritol, sorbitol, hexaglycerol, tripentaerythritol, or polyglycerol derivative. In some embodiments, the second compound further comprises one or more polyethylene glycol sections. In certain embodiments, the second compound is selected from the group consisting of ethoxylated pentaerythritol succinimidyl succinate, ethoxylated pentaerythritol succinimidyl glutarate, ethoxylated pentaerythritol succinimidyl glutaramide, ethoxylated hexaglycerol succinimidyl succinate, ethoxylated hexaglycerol succinimidyl glutarate, ethoxylated hexaglycerol succinimidyl glutaramide, and sorbitol polyglycidyl ether. In some embodiments, the molecular weight of the first compound and the second compound is between about 1000 and 20000.

In certain embodiments, the therapeutic agent is selected from the group consisting of an anticancer agent, an antiviral agent, an antibacterial agent, antifungal agent, an immunosuppressant agent, an hemostasis agent, and an anti-inflammatory agent.

In some embodiments, the gelling time of the biocompatible hydrogel polymer is controlled by the pH of the aqueous buffer. In certain embodiments, the gelling time is between about 20 seconds and 5 minutes. In some embodiments, the biocompatible hydrogel polymer gels at a target site. In certain embodiments, the biocompatible hydrogel polymer gels at a predetermined time. In some embodiments, the biocompatible hydrogel polymer is a bioabsorbable polymer. In certain embodiments, the biocompatible hydrogel polymer is bioabsorbed within about 1 to 70 days. In some embodiments, the biocompatible hydrogel polymer is substantially non-bioabsorbable. In certain embodiments, the biocompatible hydrogel polymer further comprises a radiopaque material or a pharmaceutically acceptable dye.

In some embodiments, the therapeutic agent is released from the biocompatible hydrogel polymer through diffusion, osmosis, degradation of the biocompatible hydrogel polymer, or any combination thereof. In certain embodiments, the therapeutic agent is initially released from the biocompatible hydrogel polymer through diffusion and later released through degradation of the biocompatible hydrogel polymer. In some embodiments, the therapeutic agent is substantially released from the biocompatible hydrogel polymer within 180 days. In certain embodiments, the therapeutic agent is substantially released from the biocompatible hydrogel polymer within 24 hours. In some embodiments, the first compound and the second compound do not react with the therapeutic agent during formation of the biocompatible hydrogel polymer. In certain embodiments, the biocompatible hydrogel polymer interacts with the therapeutic agent, and wherein more than 10% of the therapeutic agent is released through degradation of the biocompatible hydrogel polymer.

In a further aspect provided herein is a in vivo polymerized biocompatible hydrogel polymer comprising (a) at least one first monomeric unit bound through at least one amide, thioester, or thioether linkage to at least one second monomeric unit, (b) at least one second monomeric unit bound to at least one first monomeric unit; and (c) optionally, one or more therapeutic agents, wherein the in vivo polymerized biocompatible hydrogel polymer is polymerized at least in part at a target site in a human body.

In some embodiments, the first monomeric unit is a glycol, trimethylolpropane, pentaerythritol, hexaglycerol, or tripentaerythritol derivative. In certain embodiments, the first monomeric unit further comprises one or more polyethylene glycol sections. In some embodiments, the second monomeric unit is a trimethylolpropane, glycerol, diglycerol, pentaerythritol, sorbitol, hexaglycerol, tripentaerythritol, or polyglycerol derivative. In certain embodiments, the second monomeric unit comprises one or more polyethylene glycol sections. In some embodiments, the molecular weight of the first monomeric unit and the second monomeric unit is between about 1000 and 20000.

In certain embodiments, the therapeutic agent is selected from the group consisting of an anticancer agent, an antiviral agent, an antibacterial agent, antifungal agent, an immunosuppressant agent, an hemostasis agent, and an anti-inflammatory agent.

In some embodiments, the in vivo polymerized biocompatible hydrogel polymer gels at the target site. In certain embodiments, the in vivo polymerized biocompatible hydrogel polymer gels at a predetermined time. In some embodiments, the in vivo polymerized biocompatible hydrogel polymer is a bioabsorbable polymer. In certain embodiments, the in vivo polymerized biocompatible hydrogel polymer is bioabsorbed within about 1 to 70 days. In some embodiments, the in vivo polymerized biocompatible hydrogel polymer is substantially non-bioabsorbable. In certain embodiments, the in vivo polymerized biocompatible hydrogel polymer further comprises a radiopaque material or a pharmaceutically acceptable dye.

In some embodiments, the therapeutic agent is released from the vivo polymerized biocompatible hydrogel polymer through diffusion, osmosis, degradation of the in vivo polymerized biocompatible hydrogel polymer, or any combination thereof. In certain embodiments, the therapeutic agent is initially released from the in vivo polymerized biocompatible hydrogel polymer through diffusion and later released through degradation of the in vivo polymerized biocompatible hydrogel polymer. In some embodiments, the therapeutic agent is substantially released from the vivo polymerized biocompatible hydrogel polymer within 180 days. In certain embodiments, the therapeutic agent is substantially released from the vivo polymerized biocompatible hydrogel polymer within 24 hours.

In an additional aspect provided herein is a kit comprising (a) at least one water soluble first compound comprising more than one nucleophilic group, and one or more therapeutic agent in an aqueous buffer, and (b) at least one water soluble second compound comprising more than one electrophilic group, wherein a biocompatible hydrogel polymer is formed following mixing the first compound and the second compound in the aqueous buffer.

In a further aspect provided herein is a kit comprising (a) at least one water soluble first compound comprising more than one electrophilic group, and one or more therapeutic agent in an aqueous buffer, and (b) at least one water soluble second compound comprising more than one nucleophilic group, wherein a biocompatible hydrogel polymer is formed following mixing the first compound and the second compound in the aqueous buffer.

In another aspect provided herein is a kit for preparing a in vivo gelling pharmaceutical pre-formulation as described above, comprising (a) a first container with a first amount of the at least one first compound, (b) a second container with a second amount of the at least one second compound, (c) a third container with the aqueous buffer, (d) a mixing vessel, (e) optionally, a fourth container with a third amount of one or more therapeutic agent, (f) optionally, a fifth container with a radiopaque material or a pharmaceutically acceptable dye; and instructions for mixing the materials present in each container in the mixing vessel to produce the biocompatible hydrogel polymer, and instructions for delivering the biocompatible hydrogel polymer to the target site inside the human body.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
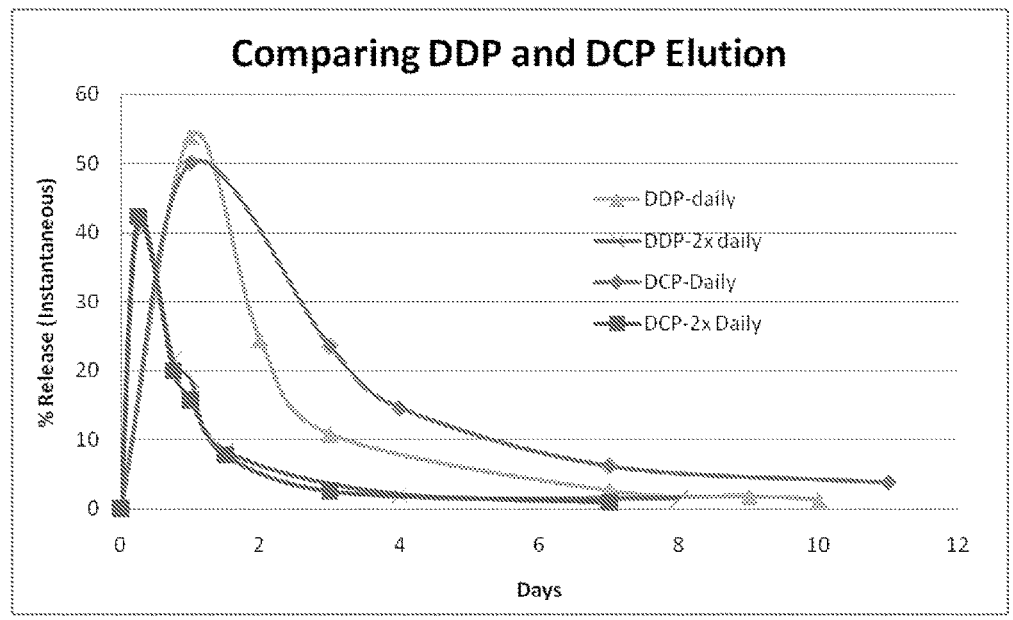
FIG. 1 shows the daily elution of carboplatin (DCP) and cisplatin (DDP) in PBS buffer using one buffer change per day (daily) or two buffer changes per day (2× daily).

Most pharmaceutical therapeutic agents are administered systemically, exposing many cells in the body to the therapeutic agent in addition to the cells at a target site (e.g., in an organ). Targeted localized drug delivery directly to a target site limits exposure to the therapeutic agents to the areas surrounding the target site. In certain instances, eliminating the introduction agents in the systemic blood stream greatly reduces or completely eliminates the side effects associated with systemic treatments and substantially improves the quality of life and life expectancy of patients. In some instances, treatments are more effective because dosages can be increased with less concern for adverse side effects. In further instances, extended release of the therapeutic agent also reduces the number of doses necessary in the course of treatment.

An in vivo gelling pre-formulation to form a biocompatible hydrogel polymer enables the administration of medication directly to target sites. The polymer starts out as a liquid pre-formulation and is delivered, together with one or more optional therapeutic agents, to the site of a disease using minimally invasive techniques. The initial liquid state allows the polymer/drug combination to be delivered through small catheters directed by endoscopes or other image guided techniques to the site of the disease (e.g., bronchoscope for lung, thoracoscope for the chest cavity, laparoscope for the abdominal cavity, cystoscope for the bladder, arthroscope for joint space, etc.). Once in the body, the liquid pre-formulation polymerizes into a solid hydrogel that in some instances adheres to the tissue and keeps the polymer/drug combination at the site of the disease. In some instances, polymerization and degradation times are controlled by varying the composition of the monomers and buffers allowing for the appropriate application and placement of the hydrogel polymer. In some embodiments, the drug is released in a precise and consistent manner. In certain instances, the biocompatible hydrogel polymer is bioabsorbed over a defined period of time. This controlled gelling and biodegradation allows the use of the biocompatible hydrogel polymer to deliver one or more therapeutic agents directly to the tissue affected by a disease, thereby minimizing systemic exposure to the therapeutic agent. Furthermore, the in vivo-gelling pre-formulation allows the placement of the hydrogel at target sites inside a human body to seal a fistula in an internal organ, close passageways or wounds.

In certain instances, local delivery of a therapeutic agent directly to a target using a biocompatible hydrogel polymer achieves the therapeutic effects of the therapeutic agent but without the side effects generally associated with systemic exposure in standard (e.g., oral or parenteral) treatment with the therapeutic agent. In certain embodiments, exposure to the therapeutic agent is limited to the tissue around the target site. In some embodiments, the patient is not exposed systemically to the therapeutic agent. In certain embodiments, a biocompatible hydrogel polymer or in vivo gelling pharmaceutical pre-formulation is used to deliver a therapeutic agent to a target site.

In some instances, the amount of the therapeutic agent, which is delivered to the target site, is increased significantly over standard systemic therapy but with minimal risk of side effects. In some embodiments, the release of therapeutic agents is sustained over longer periods of time than when the therapeutic agent is delivered systemically. In certain embodiments, the local exposure of the tissue at the target site is higher when the therapeutic agent is released from the hydrogel polymer formulation than when the therapeutic agent is delivered systemically. Because the risk of side effects due to the therapeutic agent is reduced, in certain instances, the treatment can be performed in an outpatient department at lower cost than traditional inpatient treatment with systemically delivered chemotherapeutic anticancer agents.

Exemplary Hydrogel Components

Provided herein are in vivo gelling pharmaceutical pre-formulations, comprising at least one water soluble first compound comprising more than one nucleophilic group, at least one water soluble second compound comprising more than one electrophilic group, an aqueous buffer in the pH range of 5.0 to 9.0, and optionally one or more therapeutic agents. In certain embodiments, the in vivo gelling pharmaceutical pre-formulation forms a biocompatible hydrogel polymer at a target site in a human body by mixing the at least one first compound, the at least one second compound, and the optional therapeutic agent in the aqueous buffer and delivering the mixture to the target site such that the biocompatible hydrogel polymer at least in part polymerizes and gels at the target site. In some embodiments, the biocompatible hydrogel polymer is formed following mixing the first compound and the second compound in the aqueous buffer; and wherein the biocompatible hydrogel polymer gels at a target site. In certain embodiments, mixing the first compound, the second compound, and the optional therapeutic agent in the aqueous buffer and delivering the mixture to a target site in the human body generates the in vivo gelling pharmaceutical pre-formulation such that the in vivo gelling pharmaceutical pre-formulation at least in part polymerizes and gels at the target site to form a biocompatible hydrogel polymer.

In some embodiments, the first or second compound comprising more than one nucleophilic or electrophilic group are polyol derivatives. In certain embodiments, the first or second compound is a dendritic polyol derivative. In some embodiments, the first or second compound is a glycol, trimethylolpropane, glycerol, diglycerol, pentaerythritol, sorbitol, hexaglycerol, tripentaerythritol, or polyglycerol derivative. In certain embodiments, the first or second compound is a glycol, trimethylolpropane, pentaerythritol, hexaglycerol, or tripentaerythritol derivative. In some embodiments, the first or second compound is a trimethylolpropane, glycerol, diglycerol, pentaerythritiol, sorbitol, hexaglycerol, tripentaerythritol, or polyglycerol derivative. In some embodiments, the first or second compound is a pentaerythritol, di-pentaerythritol, or tri-pentaerythritol derivative. In certain embodiments, the first or second compound is a hexaglycerol (2-ethyl-2-(hydroxymethyl)-1,3-propanediol, trimethylolpropane) derivative. In some embodiments, the first or second compound is a sorbitol derivative. In certain embodiments, the first or second compound is a glycol, propyleneglycol, glycerin, diglycerin, or polyglycerin derivative.

In some embodiments, the first and/or second compound further comprises polyethylene glycol (PEG) chains comprising one to 200 ethylene glycol subunits. In certain embodiments, the first and/or second compound further comprises polypropylene glycol (PPG) chains comprising one to 200 propylene glycol subunits.

Exemplary Nucleophilic Monomers

The in vivo gelling pharmaceutical pre-formulation comprises at least one water soluble first compound comprising more than one nucleophilic group. In some embodiments, the nucleophilic group is a hydroxyl, thiol, or amino group. In preferred embodiments, the nucleophilic group is a thiol or amino group.

In certain embodiments, the nucleophilic group is connected to the polyol derivative through a suitable linker. Suitable linkers include, but are not limited to, esters or ethers. In some instances, monomers comprising ester linkers are more susceptible to biodegradation. Examples of linkers comprising a nucleophilic group include, but are not limited to, mercaptoacetate, aminoacetate (glycin) and other amino acid esters (e.g., alanine, β-alanine, lysine, ornithine), 3-mercaptopropionate, ethylamine ether, or propylamine ether. In some embodiments, the polyol core derivative is bound to a polyethylene glycol or polypropylene glycol subunit, which is connected to the linker comprising the nucleophilic group. The molecular weight of the water soluble first compound (the nucleophilic monomer) is about 500 to 40000. In certain embodiments, the molecular weight of a water soluble first compound (a nucleophilic monomer) is about 500, about 1000, about 2000, about 3000, about 4000, about 5000, about 6000, about 7000, about 8000, about 9000, about 10000, about 12000, about 15000, about 20000, about 25000, about 30000, about 35000, or about 40000. In some embodiments, the molecular weight of a water soluble first compound is about 500 to 2000. In certain embodiments, the molecular weight of a water soluble first compound is about 15000 to about 25000.

Examples of the construction of monomers comprising more than one nucleophilic group are shown below with a trimethylolpropane or pentaerythritol core polyol. The compounds shown have thiol or amine electrophilic groups that are connected to variable lengths PEG subunit through acetate, propionate or ethyl ether linkers (ETTMP, 4ARM-PEG-NH2 and 4ARM-PEG-AA). Monomers using other polyol cores are constructed in a similar way.

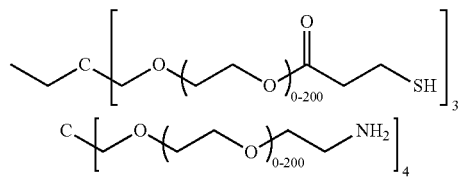

-continued

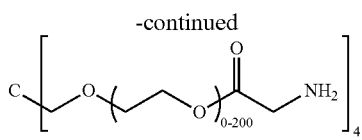

Suitable first compounds comprising a nucleophilic group (used in the amine-ester chemistry) include, but are not limited to, pentaerythritol polyethylene glycol amine (4ARM-PEG-NH2) (molecular weight selected from about 5000 to about 40000, e.g., 5000, 10000, or 20000), pentaerythritol polyethylene glycol amino acetate (4ARM-PEG-AA) (molecular weight selected from about 5000 to about 40000, e.g., 5000, 10000, or 20000), hexaglycerin polyethylene glycol amine (8ARM-PEG-NH2) (molecular weight selected from about 5000 to about 40000, e.g., 10000, 20000, or 40000), or tripentaerythritol glycol amine (8ARM(TP)-PEG-NH2) (molecular weight selected from about 5000 to about 40000, e.g., 10000, 20000, or 40000). Within this class of compounds, 4 (or 8)ARM-PEG-AA comprises ester (or acetate) groups while the 4 (or 8)ARM-PEG-NH2 monomers do not comprise ester (or acetate) groups.

Other suitable first compounds comprising a nucleophilic group (used in the thiol-ester chemistry) include, but not limited to, glycol dimercaptoacetate (THIOCURE® GDMA), trimethylolpropane trimercaptoacetate (THIOCURE® TMPMA), pentaerythritol tetramercaptoacetate (THIOCURE® PETMA), glycol di-3-mercaptopropionate (THIOCURE® GDMP), trimethylolpropane tri-3-mercaptopropionate (THIOCURE® TMPMP), pentaerythritol tetra-3-mercaptopropionate (THIOCURE® PETMP), polyol-3-mercaptopropionates, polyester-3-mercaptopropionates, propyleneglycol 3-mercaptopropionate (THIOCURE® PPGMP 800), propyleneglycol 3-mercaptopropionate (THIOCURE® PPGMP 2200), ethoxylated trimethylolpropane tri-3-mercaptopropionate (THIOCURE® ETTMP 700), and ethoxylated trimethylolpropane tri-3-mercaptopropionate (THIOCURE® ETTMP 1300).

Exemplary Electrophilic Monomers

The in vivo gelling pharmaceutical pre-formulation comprises at least one water soluble first compound comprising more than one electrophilic group. In some embodiments, the electrophilic group is an epoxide, maleimide, succinimidyl, or an alpha-beta unsaturated ester. In preferred embodiments, the electrophilic group is an epoxide or succinimidyl.

In certain embodiments, the electrophilic group is connected to the polyol derivative through a suitable linker. Suitable linkers include, but are not limited to, esters, amides, or ethers. In some instances, monomers comprising ester linkers are more susceptible to biodegradation. Examples of linkers comprising an electrophilic group include, but are not limited to, succinimidyl succinate, succinimidyl glutarate, succinimidyl succinamide, succinimidyl glutaramide, or glycidyl ether. In some embodiments, the polyol core derivative is bound to a polyethylene glycol or polypropylene glycol subunit, which is connected to the linker comprising the electrophilic group. The molecular weight of the water soluble second compound (the electrophilic monomer) is about 500 to 40000. In certain embodiments, the molecular weight of a water soluble second compound (an electrophilic monomer) is about 500, about 1000, about 2000, about 3000, about 4000, about 5000, about 6000, about 7000, about 8000, about 9000, about 10000, about 12000, about 15000, about 20000, about 25000, about 30000, about 35000, or about 40000. In some embodiments, the molecular weight of a water soluble second compound is about 500 to 2000. In certain embodiments, the molecular weight of a water soluble second compound is about 15000 to about 25000.

Examples of the construction of monomers comprising more than one electrophilic group are shown below with a pentaerythritol core polyol. The compounds shown have a succinimidyl electrophilic group, a glutarate or glutaramide linker, and a variable lengths PEG subunit (4ARM-PEG-SG and 4ARM-PEG-SGA). Monomers using other polyol cores or different linkers (e.g., succinate (SS) or succinamide (SSA)) are constructed in a similar way.

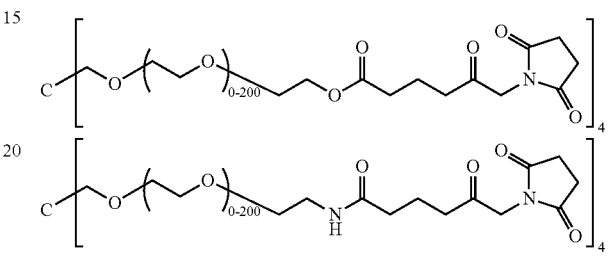

Suitable second compounds comprising an electrophilic group include, but are not limited to, pentaerythritol polyethylene glycol maleimide (4ARM-PEG-MAL) (molecular weight selected from about 5000 to about 40000, e.g., 10000 or 20000), pentaerythritol polyethylene glycol succinimidyl succinate (4ARM-PEG-SS) (molecular weight selected from about 5000 to about 40000, e.g., 10000 or 20000), pentaerythritol polyethylene glycol succinimidyl glutarate (4ARM-PEG-SG) (molecular weight selected from about 5000 to about 40000, e.g., 10000 or 20000), pentaerythritol polyethylene glycol succinimidyl glutaramide (4ARM-PEG-SGA) (molecular weight selected from about 5000 to about 40000, e.g., 10000 or 20000), hexaglycerin polyethylene glycol succinimidyl succinate (8ARM-PEG-SS) (molecular weight selected from about 5000 to about 40000, e.g., 10000 or 20000), hexaglycerin polyethylene glycol succinimidyl glutarate (8ARM-PEG-SG) (molecular weight selected from about 5000 to about 40000, e.g., 10000, 15000, 20000, or 40000), hexaglycerin polyethylene glycol succinimidyl glutaramide (8ARM-PEG-SGA) (molecular weight selected from about 5000 to about 40000, e.g., 10000, 15000, 20000, or 40000), tripentaerythritol polyethylene glycol succinimidyl succinate (8ARM(TP)-PEG-SS) (molecular weight selected from about 5000 to about 40000, e.g., 10000 or 20000), tripentaerythritol polyethylene glycol succinimidyl glutarate (8ARM(TP)-PEG-SG) (molecular weight selected from about 5000 to about 40000, e.g., 10000, 15000, 20000, or 40000), or tripentaerythritol polyethylene glycol succinimidyl glutaramide (8ARM(TP)-PEG-SGA) (molecular weight selected from about 5000 to about 40000, e.g., 10000, 15000, 20000, or 40000). The 4 (or 8)ARM-PEG-SG monomers comprise ester groups, while the 4 (or 8)ARM-PEG-SGA monomers do not comprise ester groups.

Other suitable second compounds comprising an electrophilic group are sorbitol polyglycidyl ethers, including, but not limited to, sorbitol polyglycidyl ether (DENACOL® EX-611), sorbitol polyglycidyl ether (DENACOL® EX-612), sorbitol polyglycidyl ether (DENACOL® EX-614), sorbitol polyglycidyl ether (DENACOL® EX-614 B), polyglycerol polyglycidyl ether (DENACOL® EX-512), polyglycerol polyglycidyl ether (DENACOL® EX-521), diglycerol polyglycidyl ether (DENACOL® EX-421), glycerol polyglycidyl ether (DENACOL® EX-313), glycerol polyglycidyl ether (DENACOL® EX-313), trimethylolpropane polyglycidyl ether (DENACOL® EX-321), sorbitol polyglycidyl ether (DENACOL® EJ-190), Formation of Hydrogels In certain embodiments, the first and second compounds comprising more than one nucleophilic or more than one electrophilic group safely undergo polymerization at a target site inside a mammalian body, for instance on or in an organ, inside a mammalian lung, or inside a joint. In some embodiments, the first compound and the second compound are monomers forming a polymer through the reaction of a nucleophilic group in the first compound with the electrophilic group in the second compound. In certain embodiments, the monomers are polymerized at a predetermined time. In some embodiments, the monomers are polymerized under mild and nearly neutral pH conditions. In certain embodiments, the hydrogel polymer does not change volume after curing.

In some embodiments, the first and second compound react to form amide, thioester, or thioether bonds. When a thiol nucleophile reacts with a succinimidyl electrophile, a thioester is formed. When an amino nucleophile reacts with a succinimidyl electrophile, an amide is formed.

In some embodiments, one or more first compounds comprising an amino group react with one or more second compounds comprising a succinimidyl ester group to form amide linked first and second monomer units. In certain embodiments, one or more first compounds comprising a thiol group react with one or more second compounds comprising a succinimidyl ester group to form thioester linked first and second monomer units. In some embodiments, one or more first compounds comprising an amino group react with one or more second compounds comprising an epoxide group to from amine linked first and second monomer units. In certain embodiments, one or more first compounds comprising a thiol group react with one or more second compounds comprising an epoxide group to form thioether linked first and second monomer units.

In some embodiments, a first compound is mixed with a different first compound before addition to one or more second compounds. In other embodiments, a second compound is mixed with a different second compound before addition to one or more second compounds. In certain embodiments, the properties of the in vivo gelling pharmaceutical pre-formulation and the biocompatible hydrogel polymer are controlled by the properties of the at least one first and at least one second monomer mixture. In some embodiments, one water soluble first compound is used in the biocompatible hydrogel polymer. In certain embodiments, two different water soluble first compounds are mixed and used in the biocompatible hydrogel polymer. In some embodiments, three different water soluble first compounds are mixed and used in the biocompatible hydrogel polymer. In certain embodiments, four or more different water soluble first compounds are mixed and used in the biocompatible hydrogel polymer.

In some embodiments, one water soluble second compound is used in the biocompatible hydrogel polymer. In certain embodiments, two different water soluble second compounds are mixed and used in the biocompatible hydrogel polymer. In some embodiments, three different water soluble second compounds are mixed and used in the biocompatible hydrogel polymer. In certain embodiments, four or more different water soluble second compounds are mixed and used in the biocompatible hydrogel polymer.

In some embodiments, a first compound comprising ether linkages to the nucleophilic group are mixed with a different first compound comprising ester linkages to the nucleophilic group. This allows the control of the concentration of ester groups in the resulting biocompatible hydrogel polymer. In certain embodiments, a second compound comprising ester linkages to the electrophilic group are mixed with a different second compound comprising ether linkages to the electrophilic group. In some embodiments, a second compound comprising ester linkages to the electrophilic group are mixed with a different second compound comprising amide linkages to the electrophilic group. In certain embodiments, a second compound comprising amide linkages to the electrophilic group are mixed with a different second compound comprising ether linkages to the electrophilic group.

In some embodiments, a first compound comprising an aminoacetate nucleophile is mixed with a different first compound comprising an ethylamine ether nucleophile at a specified molar ratio (x/y). In certain embodiments, the molar ratio (x/y) is 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. In certain embodiments, the mixture of two first compounds is mixed with one or more second compounds at a molar amount equivalent to the sum of x and y.

In some embodiments, the first compound comprising more than one nucleophilic group and the therapeutic agent are pre-mixed in an aqueous buffer. Once pre-mixing is complete, the second compound comprising more than one electrophilic group is added to the pre-mixture. Shortly after final mixing, the hydrogel polymer is delivered to the target site. In certain embodiments, the optional radiopaque material is added to the pre-mix, the second compound, or to the mixture just before delivery of the hydrogel polymer mixture to the target site.

In other embodiments, the second compound comprising more than one electrophilic group and the therapeutic agent are pre-mixed in an aqueous buffer. Once pre-mixing is complete, the first compound comprising more than one nucleophilic group is added to the pre-mixture. Shortly after final mixing, the hydrogel polymer is delivered to the target site. In certain embodiments, the optional radiopaque material is added to the pre-mix, the first compound, or to the mixture just before delivery of the hydrogel polymer mixture to the target site.

In some embodiments, the water soluble first compound comprising more than one nucleophilic group and the water soluble second compound comprising more than one electrophilic group are mixed together in an aqueous buffer in the pH range of 5.0 to 9.0, whereby a biocompatible hydrogel polymer is formed. In certain embodiments, the water soluble first compound comprising more than one nucleophilic group and/or the water soluble second compound comprising more than one electrophilic group are individually diluted in an aqueous buffer in the pH range of 5.0 to 9.0, wherein the individual dilutions or neat monomers are mixed, whereby a biocompatible hydrogel polymer is formed.

In certain embodiments, the concentration of the monomers in the aqueous is from about 1% to about 100%. In some embodiments, the dilution is used to adjust the viscosity of the monomer dilution. In certain embodiments, the concentration of a monomer in the aqueous buffer is about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the electrophilic and nucleophilic monomers are mixed in such ratio that there is a slight excess of electrophilic groups present in the mixture. In certain embodiments, this excess is about 10%, about 5%, about 2%, about 1%, about 0.9%, about 0.8%, about 0.7%, about 0.6%, about 0.5%, about 0.4%, about 0.3%, about 0.2%, about 0.1%, or less than 0.1%.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling pharmaceutical pre-formulation. In certain embodiments, temperature influences the gelling time of the in vivo gelling pharmaceutical pre-formulation. In some embodiments, the type of aqueous buffer influences the gelling time of the in vivo gelling pharmaceutical pre-formulation. In certain embodiments, the concentration the aqueous buffer influences the gelling time of the in vivo gelling pharmaceutical pre-formulation. In some embodiments, the nucleophilicity and/or electrophilicity of the nucleophilic and electrophilic groups of the monomers influences the gelling time of the in vivo gelling pharmaceutical pre-formulation.

In some embodiments, the gelling time or curing time of the biocompatible hydrogel polymer is controlled by the pH of the aqueous buffer. In certain embodiments, the gelling time is between about 20 seconds and 5 minutes. In some embodiments, the gelling time is less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.4 minutes, less than 1.2 minutes, less than 1.0 minutes, less than 0.8 minutes, less than 0.6 minutes, or less than 0.4 minutes. In certain embodiments, the pH of the aqueous buffer is from about 5 to about 9. In some embodiments, the pH of the aqueous buffer is from about 6.9 to about 7.9. In specific embodiments, the pH of the aqueous buffer is about 7.4. In some embodiments, the pH of the aqueous buffer is about 5, about 5.5, about 6.0, about 6.5, about 6.6, about 6.7, about 6.8, about 6.9, about 7.0, about 7.1, about 7.2, about 7.3, about 7.4, about 7.5, about 8.0, about 8.5, or about 9.0.

In certain embodiments, the gelling time or curing time of the biocompatible hydrogel polymer is controlled by the type of aqueous buffer. In some embodiments, the aqueous buffer is a physiologically acceptable buffer. In certain embodiments, aqueous buffers include, but are not limited to, aqueous saline solutions, phosphate buffered saline, borate buffered saline, a combination of borate and phosphate buffers wherein each component is dissolved in separate buffers, N-2-Hydroxyethylpiperazine-N'-2-hydroxypropanesulfonic acid (HEPES), 3-(N-Morpholino)propanesulfonic acid (MOPS), 2-([2-Hydroxy-1,1-bis(hydroxymethyl)ethyl]amino)ethanesulfonic acid (TES), 3-[N-tris(Hydroxy-methyl)ethylamino]-2-hydroxyethyl]-1-piperazinepropanesulfonic acid (EPPS), Tris[hydroxymethyl]-aminomethane (THAM), and Tris[hydroxymethyl]methyl aminomethane (TRIS). In some embodiments, the thiol-ester chemistry (e.g., ETTMP nucleophile with SGA or SG electrophile) is performed in borate buffer. In certain embodiments, the amine-ester chemistry (NH2 or AA nucleophile with SGA or SG electrophile) is performed in phosphate buffer.

In certain embodiments, the first compound and the second compound do not react with the therapeutic agent during formation of the biocompatible hydrogel polymer. In some embodiments, the therapeutic agent remains unchanged after polymerization of the first and second compounds (i.e., monomers). In certain embodiments, the therapeutic agent does not change the properties of the hydrogel polymer. In some embodiments, the physiochemical properties of the therapeutic agent and the hydrogel polymer formulation are not affected by the polymerization of the monomers.

In some embodiments, the hydrogel polymer formulations further comprise a contrast agent for visualizing the hydrogel polymer formulation and locating a tumor using e.g., X-ray, fluoroscopy, or computed tomography (CT) imaging. In certain embodiments, the contrast agent enables the visualization of the bioabsorption of the biocompatible hydrogel polymer. In some embodiments, the contrast agent is a radiopaque material. In certain embodiments, the radiopaque material is selected from, but not limited to, sodium iodide, potassium iodide, and barium sulfate, VISIPAQUE®, OMNIPAQUE®, or HYPAQUE®, tantalum, and similar commercially available compounds, or combinations thereof. In other embodiments, the biocompatible hydrogel polymer further comprises a pharmaceutically acceptable dye.

Area of for Treatment—Target Sites

In certain embodiments, the target site is inside a mammal. In some embodiments, the target site is inside a human being. In certain embodiments, the target site is on the human body. In some embodiments, the target site is accessible through surgery. In certain embodiments, the target site is accessible through minimally invasive surgery. In some embodiments, the target site is accessible through an endoscopic device. In certain embodiments, the target site is in or on a lung, in a joint, in the abdomen, in the ovary, bladder, intestine, or blood vessel.

In other embodiments, an in vivo gelling pharmaceutical pre-formulation or a biocompatible hydrogel polymer is used as a sealant or adhesive with or without a therapeutic agent. In certain embodiments, the in vivo gelling pharmaceutical pre-formulation or biocompatible hydrogel polymer is used to seal fistulas in organs inside the human body. In other embodiments, the in vivo gelling pharmaceutical pre-formulation or biocompatible hydrogel polymer is used to fill cavities in the human body.

Delivery of the Hydrogel Formulation to a Target Site

In some embodiments, the in vivo gelling pharmaceutical pre-formulation is delivered as an in vivo gelling pharmaceutical pre-formulation to a target site through a catheter or a needle to form a biocompatible hydrogel polymer at the target site. In certain embodiments, the needle or catheter is attached or part of a delivery device. In some embodiments, the in vivo gelling pharmaceutical pre-formulation containing an optional therapeutic agent is delivered to a target site and deposited on tissue at the target site. In certain embodiments, the in vivo gelling pharmaceutical pre-formulation containing an optional therapeutic agent is delivered to the site of the tumor through a catheter and sprayed onto the target tissue as a thin film using e.g. a nozzle attachment. In some embodiments, the biocompatible hydrogel polymer is directly injected into tissue at the target site.

In certain embodiments, delivery of the in vivo gelling pharmaceutical pre-formulation to the target site is minimally invasive. In some embodiments, the delivery of the in vivo gelling pharmaceutical pre-formulation to the target site in the body of a subject is image guided, using, for example, X-ray, fluoroscopy, computerized tomography (CT), magnetic resonance imaging (MRI), ultrasound (US), positron emission tomography (PET), single photon emission computed tomography (SPECT), or multimodal imaging methods. In some embodiments, the in vivo gelling pharmaceutical pre-formulation further comprises a contrast agent for visualizing the hydrogel formulation and locating a target site using e.g., X-ray, fluoroscopy, or computed tomography (CT) imaging. In certain embodiments, the contrast agent is radiopaque.

In other embodiments, the in vivo gelling pharmaceutical pre-formulation is delivered to the target site in the body using a catheter attached or integrated into an endoscopic delivery device employing fiber-optics for visualization like, for example, a bronchoscope, pleurascope, or thoracoscope. In some embodiments, a delivery device is used to deliver the in vivo gelling pharmaceutical pre-formulation to the site of the cancer. In certain embodiments, the delivery device is an endoscopic device. In some embodiments, the endoscopic device is a bronchoscope. In certain embodiments, the bronchoscope is navigated to a tumor location in the lung of a mammal. In some embodiments, the in vivo gelling pharmaceutical pre-formulation containing the therapeutic agent is delivered through a catheter attached to the bronchoscope or other endoscopic delivery device. In some embodiments, the catheter has an outer diameter of about 4 mm, about 3.8 mm, about 3.6 mm, about 3.4 mm, about 3.2 mm, about 3.0 mm, about 2.8 mm, about 2.6 mm, about 2.4 mm, about 2.2 mm, about 2.0 mm, about 1.8 mm, about 1.6 mm, about 1.4 mm, about 1.2 mm, about 1.0 mm, about 0.8 mm, or about 0.6 mm. In preferred embodiments, the catheter has an outer diameter of about 1.2 mm. In certain embodiments, the viscosity of the in vivo gelling pharmaceutical pre-formulation is close to the viscosity of water when delivering the mixture to the site of the tumor through the catheter. In some embodiments, the in vivo gelling pharmaceutical pre-formulation forming the biocompatible hydrogel further comprises a pharmaceutically acceptable dye for visualizing the hydrogel pre-formulation and locating it at a target site using an endoscopic technique.

In certain embodiments, between 10 and 30 mL of the in vivo gelling pharmaceutical pre-formulation optionally comprising a therapeutic agent is delivered to a target site. In some embodiments, about 120 mL, about 110 mL, about 100 mL, about 90 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, about 15 mL, about 10 mL, about 5 mL, about 2 mL, or about 1 mL in vivo gelling pharmaceutical pre-formulation optionally comprising a therapeutic agent is delivered to a target site. In certain embodiments, less than 120 mL, less than 110 mL, less than 100 mL, less than 90 mL, less than 80 mL, less than 75 mL, less than 70 mL, less than 65 mL, less than 60 mL, less than 55 mL, less than 50 mL, less than 45 mL, less than 40 mL, less than 35 mL, less than 30 mL, less than 25 mL, less than 20 mL, less than 15 mL, less than 10 mL, less than 5 mL, less than 2 mL, or less than 1 mL in vivo gelling pharmaceutical pre-formulation optionally comprising a therapeutic agent is delivered to a target site. In some embodiments, more than 120 mL, more than 110 mL, more than 100 mL, more than 90 mL, more than 80 mL, more than 75 mL, more than 70 mL, more than 65 mL, more than 60 mL, more than 55 mL, more than 50 mL, more than 45 mL, more than 40 mL, more than 35 mL, more than 30 mL, more than 25 mL, more than 20 mL, more than 15 mL, more than 10 mL, more than 5 mL, more than 2 mL, or more than 1 mL in vivo gelling pharmaceutical pre-formulation optionally comprising a therapeutic agent is delivered to a target site. In certain embodiments, about 5 to 50 mL in vivo gelling pharmaceutical pre-formulation optionally comprising a therapeutic agent is delivered to a target site.

In some embodiments, the gelling time of the biocompatible hydrogel polymer is set according to the preference of the doctor delivering the hydrogel polymer mixture to the site of the cancer. In most instances, a physician delivers the hydrogel polymer mixture to the site of the cancer within 15 to 30 seconds. In some embodiments, the hydrogel polymer mixture gels after delivery at the site of the cancer, covering the tumor.

In some embodiments, the gelling time or curing time of the biocompatible hydrogel polymer is controlled by the pH of the aqueous buffer. In certain embodiments, the gelling time is between about 20 seconds and 5 minutes. In preferred embodiments, the gelling time is about 90 seconds. In some embodiments, the gelling time is less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.5 minutes, less than 1.4 minutes, less than 1.2 minutes, less than 1.0 minutes, less than 0.8 minutes, less than 0.6 minutes, or less than 0.4 minutes. In certain embodiments, the gelling time is more than 5 minutes, more than 4.8 minutes, more than 4.6 minutes, more than 4.4 minutes, more than 4.2 minutes, more than 4.0 minutes, more than 3.8 minutes, more than 3.6 minutes, more than 3.4 minutes, more than 3.2 minutes, more than 3.0 minutes, more than 2.8 minutes, more than 2.6 minutes, more than 2.4 minutes, more than 2.2 minutes, more than 2.0 minutes, more than 1.8 minutes, more than 1.6 minutes, more than 1.5 minutes, more than 1.4 minutes, more than 1.2 minutes, more than 1.0 minutes, more than 0.8 minutes, more than 0.6 minutes, or more than 0.4 minutes. In some embodiments, the gelling time is about 5 minutes, about 4.8 minutes, about 4.6 minutes, about 4.4 minutes, about 4.2 minutes, about 4.0 minutes, about 3.8 minutes, about 3.6 minutes, about 3.4 minutes, about 3.2 minutes, about 3.0 minutes, about 2.8 minutes, about 2.6 minutes, about 2.4 minutes, about 2.2 minutes, about 2.0 minutes, about 1.8 minutes, about 1.6 minutes, about 1.5 minutes, about 1.4 minutes, about 1.2 minutes, about 1.0 minutes, about 0.8 minutes, about 0.6 minutes, or about 0.4 minutes.

In certain embodiments, the pH of the aqueous buffer is from about 5 to about 9. In some embodiments, the pH of the aqueous buffer is from about 6.9 to about 7.9. In specific embodiments, the pH of the aqueous buffer is about 7.4. In some embodiments, the pH is about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling pharmaceutical pre-formulation.

In some embodiments, curing of the biocompatible hydrogel polymer is verified post-administration. In certain embodiments, the verification is performed in vivo at the delivery site. In other embodiments, the verification is performed ex vivo. In some embodiments, curing of the biocompatible hydrogel polymer is verified visually through the fiber-optics of an endoscopic device. In certain embodiments, curing of biocompatible hydrogel polymers comprising radiopaque materials is verified using X-ray, fluoroscopy, or computed tomography (CT) imaging. A lack of flow of the biocompatible hydrogel polymer indicates that the biocompatible hydrogel polymer has gelled and the hydrogel is sufficiently cured. In further embodiments, curing of the biocompatible hydrogel polymer is verified by evaluation of the residue in the delivery device, for instance the residue in the catheter of the bronchoscope or other endoscopic device, or the residue in the syringe used to deliver the biocompatible hydrogel polymer. In other embodiments, curing of the biocompatible hydrogel polymer is verified by depositing a small sample (e.g., ~1 mL) on a piece of paper or in a small vessel and subsequent evaluation of the flow characteristics after the gelling time has passed.

In some embodiments, the in vivo gelling pharmaceutical pre-formulation optionally comprising one or more therapeutic agents is delivered to the target site so that the pre-formulation mostly covers the target site. In certain embodiments, the in vivo gelling pharmaceutical pre-formulation substantially covers an exposed portion of diseased tissue. In some embodiments, the in vivo gelling pharmaceutical pre-formulation does not spread to any other location intentionally. In some embodiments, the in vivo gelling pharmaceutical pre-formulation substantially covers diseased tissue and does not significantly cover healthy tissue. In certain embodiments, the biocompatible hydrogel polymer does not significantly cover healthy tissue. In some embodiments, in vivo gelling pharmaceutical pre-formulation gels over the target site and thoroughly covers diseased tissue. In some embodiments, the biocompatible hydrogel polymer adheres to tissue.

Control of Release Rate of a Therapeutic Agent

In some embodiments, the biocompatible hydrogel polymer slowly delivers a therapeutic agent to a target site by diffusion and/or osmosis over time ranging from hours to days. In certain embodiments, the drug is delivered directly to the target site. In some embodiments, the procedure of delivering a biocompatible hydrogel polymer comprising a therapeutic agent to a target site is repeated several times, if needed. In other embodiments, the therapeutic agent is released from the biocompatible hydrogel polymer through biodegradation of the hydrogel polymer. In some embodiments, the therapeutic agent is released through a combination of diffusion, osmosis, and/or hydrogel degradation mechanisms. In certain embodiments, the release profile of the therapeutic agent from the hydrogel polymer is unimodal. In some embodiments, the release profile of the therapeutic agent from the hydrogel polymer is bimodal. In certain embodiments, the release profile of the therapeutic agent from the hydrogel polymer is multimodal.

In some embodiments, the therapeutic agent is released from the biocompatible hydrogel polymer though diffusion or osmosis. In certain embodiments, the therapeutic agent is substantially released from the biocompatible hydrogel polymer within 180 days. In some embodiments, the therapeutic agent is substantially released from the biocompatible hydrogel polymer within 14 days. In certain embodiments, the therapeutic agent is substantially released from the biocompatible hydrogel polymer within 24 hours. In some embodiments, the therapeutic agent is substantially released from the biocompatible hydrogel polymer within one hour. In certain embodiments, the therapeutic agent is substantially released from the biocompatible hydrogel polymer within about 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, about 1 day, about 0.5 day, about 6 hours, about 4 hours, about 2 hours, about or 1 hour. In some embodiments, the therapeutic agent is substantially released from the biocompatible hydrogel polymer within more than 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, more than 1 day, more than 0.5 day, more than 6 hours, more than 4 hours, more than 2 hours, more than or 1 hour. In certain embodiments, the therapeutic agent is substantially released from the biocompatible hydrogel polymer within less than 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, less than 1 day, less than 0.5 day, less than 6 hours, less than 4 hours, less than 2 hours, less than or 1 hour. In some embodiments, the therapeutic agent is substantially released from the biocompatible hydrogel polymer within about one day to about fourteen days. In certain embodiments, the therapeutic agent is substantially released from the biocompatible hydrogel polymer within about one day to about 70 days.

Bioabsorbance of the Hydrogel

In some embodiments, the biocompatible hydrogel polymer is a bioabsorbable polymer. In certain embodiments, the biocompatible hydrogel polymer is bioabsorbed within about 5 to 30 days. In some embodiments, the biocompatible hydrogel polymer is bioabsorbed within about 30 to 180 days. In preferred embodiments, the biocompatible hydrogel polymer is bioabsorbed within about 1 to 7r0 days. In some embodiments the biocompatible hydrogel polymer is bioabsorbed within about 365 days, 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, or about 1 day. In certain embodiments the biocompatible hydrogel polymer is bioabsorbed within less than 365 days, 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, or less than 1 day. In some embodiments the biocompatible hydrogel polymer is bioabsorbed within more than 365 days, 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, or more than 1 day. In some embodiments, the biocompatible hydrogel polymer is substantially non-bioabsorbable.

The biocompatible hydrogel polymer is slowly bioabsorbed, dissolved, and or excreted. In some instances, the rate of bioabsorption is controlled by the number of ester groups in the biocompatible and/or biodegradable hydrogel polymer. In other instances, the higher the concentration of ester units is in the biocompatible hydrogel polymer, the longer is its lifetime in the body. In further instances, the electron density at the carbonyl of the ester unit controls the lifetime of the hydrogel polymer in the body. In certain instances, biocompatible hydrogel polymers without ester groups are essentially not biodegradable. In additional instances, the molecular weight of the first and second compounds controls the lifetime of the hydrogel polymer in the body. In further instances, the number of ester groups per gram of polymer controls the lifetime of the hydrogel polymer in the body.

In some instances, the lifetime of the hydrogel polymer can be estimated using a model, which controls the temperature and pH at physiological levels while exposing the hydrogel polymer to a buffer solution. In certain instances, the biodegradation of the hydrogel polymer is substantially non-enzymatic degradation.

Target Diseases for Treatment with Biocompatible Hydrogel Polymer

In some embodiments, the biocompatible hydrogel polymer does not contain biological materials like fibrin and does not pose a risk of allergic reactions. In some embodiments, the biocompatible hydrogel polymer does not comprise a therapeutic agent. In certain embodiments, a biocompatible hydrogel polymer not comprising a therapeutic agent is used in the treatment of fistulas. The in vivo gelling pharmaceutical pre-formulation is delivered to the site of a fistula to seal the fistula by forming a biocompatible hydrogel polymer to cover the hole. In some embodiments, the fistulas that are treated with the biocompatible hydrogel polymer are for example, bronchopleural, enterocutaneous, enterovesicular, or enterovaginal fistulas. In certain embodiments, the in vivo gelling pharmaceutical pre-formulation is delivered through an endoscopic device (e.g., a bronchoscope or thoracoscope). In other embodiments, the biocompatible hydrogel polymer used in the treatment of fistulas comprises optional therapeutic agents, for example antibiotics and anti-inflammatory agents. Incorporation of antibiotics and anti-inflammatory agents is useful for fistula repair, for example in Crohn's disease or other fistulas in contaminated places. In some embodiments, a biocompatible hydrogel polymer not comprising a therapeutic agent is used in lung volume reduction in the treatment of for example COPD or emphysema. The in vivo gelling pharmaceutical pre-formulation is delivered to a target site in the lung to controllably collapse a part of the lung. In other embodiments, a biocompatible hydrogel polymer not comprising a therapeutic agent is used as a lubricant for joint disease. In certain embodiments, a biocompatible hydrogel polymer not comprising a therapeutic agent is used to seal wounds.

In certain embodiments, the biocompatible hydrogel polymer comprises a therapeutic agent. In some embodiments, the biocompatible hydrogel polymer and in vivo gelling pharmaceutical pre-formulation is used to deliver a therapeutic agent to a target site. In certain embodiments, the target site is the site of a tumor or cancer. In some embodiments, the biocompatible hydrogel polymer comprising a therapeutic agent is used in the treatment of cancers using one or more anticancer agents. In certain embodiments, the cancer is a cancer of the lung (e.g., NSCLC, mesothelioma), ovary, bladder, or colon. In some embodiments, a biocompatible hydrogel polymer comprising a therapeutic agent is used in locoregional control for advanced lung cancer in patients unable to tolerate conventional chemotherapy. In certain embodiments, a biocompatible hydrogel polymer comprising a therapeutic agent is used in neoadjuvant chemotherapy for patients with stage III disease. In some embodiments, a biocompatible hydrogel polymer comprising a therapeutic agent is used in the treatment of solitary lung metastases from other malignancies in patients unable to tolerate surgery. In certain embodiments, a biocompatible hydrogel polymer comprising a therapeutic agent is used as an alternative or adjunct to systemic chemotherapy for locoregional control of lung cancer in patients. In some embodiments, the therapeutic agent is an anticancer agent. In certain embodiments, the therapeutic agent is a chemotherapeutic anticancer agent.

In some embodiments, a biocompatible hydrogel polymer comprising a therapeutic agent is used for the delivery of therapeutic agents to a target site. In certain embodiments, a biocompatible hydrogel polymer comprising a cytotoxin or chemotherapy agent is used for the delivery of the cytotoxin or chemotherapy agent to the site of a mesothelioma or other cancer. In some embodiments, a biocompatible hydrogel polymer comprising a chemotherapy agent is used for the delivery of the chemotherapy agent to the site of an ovarian cancer or peritoneal carcinomatosis. In certain embodiments, a biocompatible hydrogel polymer comprising a chemotherapy agent is used for the delivery of the chemotherapy agent to the site of a bladder cancer. In certain embodiments, a biocompatible hydrogel polymer comprising a chemotherapy agent is used for the delivery of the chemotherapy agent to the site of a colon cancer. In some embodiments, a biocompatible hydrogel polymer comprising anti-inflammatory agents, anesthetics, and/or analgesics is used in the treatment of arthritis (e.g., rheumatoid arthritis or osteoarthritis). In certain embodiments, a biocompatible hydrogel polymer comprising antibiotics is used for the delivery of the antibiotics in the treatment of tuberculosis (e.g., multi-drug resistant tuberculosis). In some embodiments, a biocompatible hydrogel polymer comprising antifungals is used in the treatment of aspergillosis or other localized pulmonary fungal infections. In certain embodiments, a biocompatible hydrogel polymer comprising antibiotics and/or anti-inflammatory agents is used for fistula repair in Crohn's disease and other fistulas in contaminated places. In some embodiments, a biocompatible hydrogel polymer comprising one or more antibiotics is used for the long term release of antibiotics for prosthetic join infections. In certain embodiments, a biocompatible hydrogel polymer comprising one or more antibiotics is used in antibiotic prophylaxis in abdominal surgery. In some embodiments, a biocompatible hydrogel polymer comprising a hemostasis agent is used to control bleeding (e.g., to control gastrointestinal bleeding or endobronchial bleeding).

Exemplary Anticancer Agents

In some embodiments, the anticancer agent is a chemotherapeutic anticancer agent. In certain embodiments, the biocompatible hydrogel polymer is loaded with a desired amount of one or more chemotherapeutic anticancer agents to form a biocompatible hydrogel chemopolymer. Examples of chemotherapeutic anticancer agents include, but are not limited to, Nitrogen Mustards like bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides like etoglucid; Other Alkylating Agents like dacarbazine, mitobronitol, pipobroman, temozolomide; Folic Acid Analogues like methotrexate, pemetrexed, pralatrexate, raltitrexed; Purine Analogs like cladribine, clofarabine, fludarabine, mercaptopurine, nelarabine, tioguanine; Pyrimidine Analogs like azacitidine, capecitabine, carmofur, cytarabine, decitabine, fluorouracil, gemcitabine, tegafur; Vinca Alkaloids like vinblastine, vincristine, vindesine, vinflunine, vinorelbine; Podophyllotoxin Derivatives like etoposide, teniposide; Colchicine derivatives like demecolcine; Taxanes like docetaxel, paclitaxel, paclitaxel poliglumex; Other Plant Alkaloids and Natural Products like trabectedin; Actinomycines like dactinomycin; Antracyclines like aclarubicin, daunorubicin, doxorubicin, epirubicin, idarubicin, mitoxantrone, pirarubicin, valrubicin, zorubincin; Other Cytotoxic Antibiotics like bleomycin, ixabepilone, mitomycin, plicamycin; Platinum Compounds like carboplatin, cisplatin, oxaliplatin, satraplatin; Methylhydrazines like procarbazine; Sensitizers like aminolevulinic acid, efaproxiral, methyl aminolevulinate, porfimer sodium, temoporfin; Protein Kinase Inhibitors like dasatinib, erlotinib, everolimus, gefitinib, imatinib, lapatinib, nilotinib, pazonanib, sorafenib, sunitinib, temsirolimus; Other Antineoplastic Agents like alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens like diethylstilbenol, ethinylestradiol, fosfestrol, polyestradiol phosphate; Progestogens like gestonorone, medroxyprogesterone, megestrol; Gonadotropin Releasing Hormone Analogs like buserelin, goserelin, leuprorelin, triptorelin; Anti-Estrogens like fulvestrant, tamoxifen, toremifene; Anti-Androgens like bicalutamide, flutamide, nilutamide; Enzyme Inhibitors like aminoglutethimide, anastrozole, exemestane, formestane, letrozole, vorozole; Other Hormone Antagonists like abarelix, degarelix; Immunostimulants like histamine dihydrochloride, mifamurtide, pidotimod, plerixafor, roquinimex, thymopentin; Immunosuppressants like everolimus, gusperimus, leflunomide, mycophenolic acid, sirolimus; Calcineurin Inhibitors like ciclosporin, tacrolimus; Other Immunosuppressants like azathioprine, lenalidomide, methotrexate, thalidomide; and Radiopharmaceuticals like iobenguane.

In preferred embodiments, the chemotherapeutic anticancer agent is selected from, but not limited to, docetaxel, paclitaxel, paclitaxel poliglumex, ixabepilone, carboplatin, cisplatin, oxaliplatin, satraplatin, etoposide, gemcitabine, or pemetrexed.

In some embodiments, the anticancer agent is a toxin, e.g. diphtheria toxin. In certain embodiments, the biocompatible hydrogel polymer is loaded with a therapeutically effective amount of one or more toxins to form a biocompatible hydrogel polymer. Examples of toxins include Exotoxins like diphtheria toxin, botulinium toxin, cytolysins, hemolysins (e.g., α-toxin or α-hemolysin of *Staphyllococcus aureus*), cholera toxin, pertussis toxin, Shiga toxin; Heat-Stable Enterotoxin from *E. coli*; Curare; α-Cobratoxin; Verotoxin-1; and Adenylate Cyclase (AC) toxin from *Bordetella pertussis*.

Exemplary Antifungals

In some embodiments, the biocompatible hydrogel polymer comprises an antifungal agent. In certain embodiments, the antifungal agent is a polyene antifungal, an imidazole, triazole, or thiazole antifungal, a triazole antifungal, a thiazole antifungal, an allylamine derivative, or an echinocandin derivative. Examples of antifungal agents include, but are not limited to, Polyene derivatives like natamycin, rimocidin, filipin, nystatin, amphotericin B, candicin, hamycin; Imidazole derivatives like miconazole, ketoconazole, clotrimazole, econazole, omoconazole, bifonazole, butoconazole, fenticonazole, isoconazole, oxiconazole, sertaconazole, sulconazole, tioconazole; Tetrazole derivatives like fluconazole, itraconazole, isavuconazole, posaconazole, voriconazole, terconazole, albaconazole; Thiazole derivatives like abafungin; Allylamine derivative like terbifine, naftifine, butenafine; Echinocandin derivatives like anidulafungin, caspofungin, micafungin; Other antifungals like polygodial, benzoic acid, ciclopirox, tonaftate, undecylenic acid, flycytosine, griseofulvin, haloprogin, sodium bicarbonate, pirctone olamine, zinc pyrithione, selenium sulfide, tar, or tea tree oil.

Exemplary Antibiotics

In some embodiments, the biocompatible hydrogel polymer comprises an antibiotic. In certain embodiments, the antibiotic agent is a aminoglycoside, ansamycin, carbacephem, carbapenem, cephalosporin, glycopeptide, lincosamide, lipopeptide, macrolide, monobactam, nitrofurans, penicillin, polypeptide, quinolone, sulfonamide, or tetracycline. Examples of antibiotic agents include, but are not limited to, Aminoglycoside derivatives like amikacin, gentamicin, kanamycin, neomycin, netilmicin, tobramicin, paromomycin; Ansamycin derivatives like geldanamycin, herbimycin; Carbacephem derivatives like loracarbef, Carbapenem derivatives like ertapenem, doripenem, imipenem, meropenem; Cephalosporin derivatives like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; Glycopeptide derivatives like teicoplanin, vancomycin, telavancin; Lincosamides like clindamycin, lincomycin; Lipopeptide derivatives like daptomycin; Macrolide derivatives like azithromycin, clarithromycin, dirithromycin, erythromycin, roxithromycin, troleandomycin; telithreomycin, spectinomycin; Monobactam derivatives like aztreonam; Nitrofuran derivatives like furazolidone, nitrofurantoin; Penicillin derivatives like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; Penicillin combinations like amoxicillin/clavulanate, ampicillin/sulbactam, piperacillin/tazobactam, ticarcillin/clavulanate; Polypeptide derivatives like bacitracin, colistin, polymyxin B; Quinolone derivatives like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; Sulfonamide derivatives like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; Tetracyclin derivatives like demeclocycline, doxycycline, minocycline, oxytetracycline, tetracycline; Derivatives against mycobacteria like clofazimine, dapsone, capreomycin, cycloserine, ethambutol, ethioamide, isoniazid, pyrazinamide, rifampin, refampicin, rifabutin, rifapentine, streptomycin; or other antibiotic agents like arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole.

Exemplary Antiviral Agents

In some embodiments, the biocompatible hydrogel polymer comprises an antiviral agent. In certain embodiments, the antiviral agent is a nucleoside reverse transcriptase inhibitor, a non-nucleoside reverse transcriptase inhibitor, a fusion inhibitor, an integrase inhibitor, a nucleoside analog, a protease inhibitor, a reverse transcriptase inhibitor. Examples of antiviral agents include, but are not limited to, abacavir, aciclovir, acyclovir, adefovir, amantadine, amprenavir, ampligen, arbidol, atazanavir, boceprevir, cidofovir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type II, interferon type I, interferon, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir (Valtrex), valganciclovir, vicriviroc, vidarabine, viramidine, zalcitabine, zanamivir, zidovudine.

Exemplary Immunosuppressive Agents

In some embodiments, the biocompatible hydrogel polymer comprises an immunosuppressive agent. In certain embodiments, the immunosuppressive agent is a calcinuerin inhibitor, mTor inhibitor, an anti-proliferative agent (e.g., an alkylating agent or an antimetabolite), a glucocorticosteroid, an antibody, or an agent acting on immunophilins. Examples of immunosuppressive agents include, but are not limited to, Calcineurin inhibitors like ciclosporin, tacrolimus; mTOR inhibitors like sirolimus, everolimus; Anti-proliferatives like azathioprine, mycophenolic acid; Corticosteroids like prednisolone, hydrocortisone; Monoclonal anti-IL-2Rα receptor antibodies like basiliximab, daclizumab; Polyclonal anti-T-cell antibodies like anti-thymocyte globulin (ATG), anti-lymphocyte globulin (ALG); Monoclonal anti-CD20 antibodies like rituximab; Interleukin inhibitors like daclizumab, basiliximab, anakinra, rilonacept, ustekinumab, mepolizumab, tocilizumab, canakinumab, briakinumab; Tumor necrosis factor alpha (TNF-α) inhibitors like etanercept, infliximab, afelimomab, adalimumab, certolizumab pegol, golimumab; Selective immunosuppressants like muromonab-CD3, antilymphocyte immunoglobulin (horse), antithymocyte immunoglobulin (rabbit), mycophenolic acid, sirolimus, leflunomide, alefacept, everolimus, gusperimus, efalizumab, abetimus, natalizumab, abatacept, eculizumab, belimumab, fingolimod, belatacept; or Other immunosuppressants like azathioprine, thalidomide, methotrexate, lenalidomide Exemplary Hemostasis Agents In some embodiments, the biocompatible hydrogel polymer comprises a hemostasis agent (or antihemorrhagic agent). In certain embodiments, the hemostasis agent is an antifibrinolytic (amino acid or proteinase inhibitor), a vitamin K, fibrinogen, a local hemostatic, or a blood coagulation factor. Examples of hemostasis agents include, but are not limited to, Amino acids like aminocaproic acid, tranexamic acid, aminomethylbenzoic acid; Proteinase inhibitors like aprotinin, alfa1 antitrypsin, C1-inhibitor, camostat; Vitamin K like phytomenadione, menadione; Fibrinogen like Human fibrinogen; Local hemostatics like absorbable gelatin sponge, oxidized cellulose, tetragalacturonic acid hydroxymethylester, adrenalone, thrombin, collagen, calcium alginate, epinephrine, human fibrinogen; Blood coagulation factors like coagulation factor IX, II, VII and X in combination, coagulation factor VIII, factor VIII inhibitor bypassing activity, coagulation factor IX, coagulation factor VII, von Willebrand factor and coagulation factor VIII in combination, coagulation factor XIII, eptacog alfa, nonacog alfa, thrombin; Other systemic hemostatics like etamsylate, carbazochrome, batroxobin, romiplostim, eltrombopag.

Exemplary Non-Steroidal Anti-Inflammatory Agents

In some embodiments, the biocompatible hydrogel polymer comprises an anti-inflammatory agent. In certain embodiments, the anti-inflammatory agent is a non-steroidal anti-inflammatory agent. In other embodiments, the anti-inflammatory agent is a glucocorticosteroid. In some embodiments, the non-steroidal anti-inflammatory agent is a butylpyrazolidine, an acetic acid derivative, oxicam, propionic acid derivative, fenamate, or coxib. Examples of anti-inflammatory agents include, but are not limited to, Butylpyrazolidines like phenylbutazone, mofebutazone, oxyphenbutazone, clofezone, kebuzone; Acetic acid derivatives and related substances like indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, indometacin combinations, diclofenac combinations; Oxicams like piroxicam, tenoxicam, droxicam, lornoxicam, meloxicam; Propionic acid derivatives like ibuprofen, naproxen, ketoprofen, fenoprofen, fenbufen, benoxaprofen, suprofen, pirprofen, flurbiprofen, indoprofen, tioprofenoic acid, oxaprozin, ibuproxam, dexibuprofen, flunoxaprofen, alminoprofen, dexketoprofen, naproxcinod; Fenamates like mefenamic acid, tolfenamic acid, flufenamic acid, meclofenamic acid; Coxibs like celecoxib, rofecoxib, valdecoxib, parecoxib, etoricoxib, lumiracoxib; Other antiinflammatory and antirheumatic agents like nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate.

Exemplary Analgesics and Anesthetics

In some embodiments, the biocompatible hydrogel polymer comprises an analgesic or anesthetic agent. In certain embodiments, the analgesic or anesthetic agent paracetamol, an opiate, diproqualone, phenazone, cocaine, or lidocaine. In certain embodiments, the opioid is a natural opium alkaloid, phenylpiperidine derivative, diphenylpropylamine derivative, benzomorphan derivative, oripavin derivative, or morphinan derivative. In some embodiments, the analgesic is a salicylic acid derivative, pyrazolone, or anilide. In other embodiments, the analgesic is an ergot alkaloid, corticosteroid derivative, or selective serotonin (5HT1) agonist. Examples of local anesthetics include, but are not limited to, Esters of aminobenzoic acid like metabutethamine, procaine, tetracaine, chloroprocaine, benzocaine; Amides like bupivacaine, lidocaine, mepivacaine, prilocaine, butanilicaine, cinchocaine, etidocaine, articaine, ropivacaine, levobupivacaine, tetracaine, chloroprocaine, benzocaine; Esters of benzoic acid like cocaine; Other local anesthetics like ethyl chloride, dyclonine, phenol, capsaicin.

Exemplary Combinations

In some embodiments, a second therapeutic agent can be incorporated into the biocompatible hydrogel polymer formulation. Provided herein are in vivo gelling pharmaceutical pre-formulations, comprising a water soluble first compound comprising more than one nucleophilic group, a water soluble second compound comprising more than one electrophilic group, a first therapeutic agent, a second therapeutic agent, and an aqueous buffer in the pH range of 5.0 to 9.0, wherein a biocompatible hydrogel polymer is formed following mixing the first compound and the second compound in the aqueous buffer; and wherein the biocompatible hydrogel polymer gels at a target site. In some embodiments, the first compound and the second compound do not react with the first and second therapeutic agent during formation of the biocompatible hydrogel polymer. In preferred embodiments, the second anticancer agent is selected from, but not limited to, docetaxel, paclitaxel, paclitaxel poliglumex, ixabepilone, carboplatin, cisplatin, oxaliplatin, satraplatin, etoposide, gemcitabine, or pemetrexed.

In certain embodiments, the biocompatible hydrogel polymer comprises two or more therapeutic agents. In some embodiments, the therapeutic agents are chemotherapeutic anticancer agents. In preferred embodiments, the therapeutic agents are selected from but not limited to, docetaxel, paclitaxel, paclitaxel poliglumex, ixabepilone, carboplatin, cisplatin, oxaliplatin, satraplatin, etoposide, gemcitabine, or pemetrexed.

In certain embodiments, the in vivo gelling pharmaceutical pre-formulations comprise additional therapeutic agents. Additional therapeutic agents include, but are not limited to, anesthetics, antibacterial compounds, antiviral compounds, immunosuppressants, anti-inflammatory compounds, anti-proliferative compounds, anti-angiogenesis compounds, or hormones.

In some embodiments, the biocompatible hydrogel polymer or in vivo gelling pre-formulations further comprise a visualization agent for visualizing the placement of the biocompatible hydrogel polymer at a target site The visualization agent assists in visualizing the placement using minimally invasive delivery, e.g., using an endoscopic device. In certain embodiments, the visualization agent is a dye. In specific embodiments, the visualization agent is colorant.

In some embodiments, the biocompatible hydrogel polymer formulations further comprise a contrast agent for visualizing the hydrogel formulation and locating a tumor using e.g., X-ray, fluoroscopy, or computed tomography (CT) imaging. In certain embodiments, the contrast agent is radiopaque. In some embodiments, the radiopaque material is selected from sodium iodide, potassium iodide, barium sulfate, VISIPAQUE®, OMNIPAQUE®, or HYPAQUE®, tantalum, and similar commercially available compounds, or combinations thereof.

Exemplary Kits

Further provided herein is a kit comprising a) a water soluble first compound comprising more than one nucleophilic group, and a therapeutic agent in an aqueous buffer; and b) a water soluble second compound comprising more than one electrophilic group; wherein a biocompatible hydrogel polymer is formed following mixing the first compound and the second compound in the aqueous buffer.

Also provided here is a kit comprising a) a water soluble first compound comprising more than one electrophilic group, and a therapeutic agent in an aqueous buffer; and b) a water soluble second compound comprising more than one nucleophilic group; wherein a biocompatible hydrogel polymer is formed following mixing the first compound and the second compound in the aqueous buffer.

Further provided herein is a kit for preparing any in vivo gelling pharmaceutical pre-formulation as described herein, comprising a first container with a first amount of the first compound, a second container with a second amount of the second compound, a third container with a third amount of the therapeutic agent, a fourth container with the aqueous buffer, a mixing vessel, optionally a fifth container with the radiopaque material, instructions for mixing the materials present in each container in the mixing vessel to produce the biocompatible hydrogel polymer, and instructions for delivering the biocompatible hydrogel polymer to the site of the cancer.

Also provided herein is a kit for preparing any in vivo gelling pharmaceutical pre-formulation as described herein, comprising a first container comprising a first amount of the first compound and a second amount of the therapeutic agent, a second container with a third amount of the second compound, a third container with the aqueous buffer, a mixing vessel, optionally a fourth container with the radiopaque material, instructions for mixing the materials present in each container in the mixing vessel to produce the biocompatible hydrogel polymer, and instructions for delivering the biocompatible hydrogel polymer to the site of the cancer.

Further provided herein is a kit for preparing any in vivo gelling pharmaceutical pre-formulation as described herein, comprising a first container comprising a first amount of the first compound, a second container with a second amount of the second compound and a third amount of the therapeutic agent, a third container with the aqueous buffer, a mixing vessel, optionally a fourth container with the radiopaque material, instructions for mixing the materials present in each container in the mixing vessel to produce the biocompatible hydrogel polymer, and instructions for delivering the biocompatible hydrogel polymer to the site of the cancer.

Additionally provided herein is a kit for preparing an in vivo gelling pharmaceutical pre-formulation comprising (a) a first container with a first amount of the at least one first compound; (b) a second container with a second amount of the at least one second compound; (c) a third container with the aqueous buffer; (d) a mixing vessel; (e) optionally, a fourth container with a third amount of one or more therapeutic agent; (f) optionally, a fifth container with the radiopaque material or dye; and instructions for mixing the materials present in each container in the mixing vessel to produce the biocompatible hydrogel polymer, and instructions for delivering the biocompatible hydrogel polymer to the target site inside the human body. In certain embodiments, the first container and the second container each are a syringe, wherein the plungers of the syringes are interconnected, and the outlets of the two syringes are connected to the mixing vessel. In some embodiments, the mixing vessel is connected to a catheter attached to an endoscopic device.

EXAMPLES

The following specific examples are to be construed as merely illustrative, and not limitative of the remainder of the disclosure in any way whatsoever.

TABLE 1

Components used in formulations.

| Components | Technical Name |
|---|---|
| 4ARM-20k-AA | 4armPEG Acetate Amine HCL Salt, MW 20000 |
| 8ARM-20k-NH2 | 8arm PEG Amine (hexaglycerol), HCl Salt, MW 20000 |
| 8ARM-15k-SG | 8arm PEG Succinimidyl Glutarate (hexaglycerol), MW 15000 |
| ETTMP-1300 | Ethoxylated Trimethylolpropane Tri(3-Mercaptopropionate) |
| 4ARM-20k-SGA | 4arm PEG Succinimidyl Glutaramide (pentaerythritol), MW 20000 |
| EJ-190 | Sorbitol polyglycidyl ether |
| DDP | cisplatin; cisdiamminedichloroplatinum(II) |
| DCP | carboplatin; cis-Diammine(1,1-cyclobutanedicarboxylato)platinum(II) |

Example 1: Manufacture of Hydrogel (Amine-Ester Chemistry)

A solution of 8ARM-20K-NH2 was prepared in a Falcon tube by dissolving about 0.13 g solid monomer in about 2.5 mL of sodium phosphate buffer (buffer pH 7.36). The mixture was shaken for about 10 seconds at ambient temperature until complete dissolution was obtained. The Falcon tube was allowed to stand at ambient temperature. In another Falcon tube, 0.10 g of 8ARM-15K-SG was dissolved in the same phosphate buffer as above. The mixture was shaken for about 10 seconds and at this point all the powder dissolved. The 8ARM-15K-SG solution was poured immediately into the 8ARM-20K-NH2 solution and a timer was started. The mixture was shaken and mixed for about 10 seconds and a 1 mL solution of the mixture was pipetted out using a mechanical high precision pipette. The gel time of 1 mL liquid was collected and then verified with the lack of flow for the remaining liquids. The get time data of the formulation was recorded and was about 1 min 30 seconds.

Example 2: Manufacture of Hydrogel (Amine-Ester Chemistry)

A solution of 8ARM-20K-NH2 was prepared in a Falcon tube by dissolving about 0.13 g solid monomer in about 5 mL of sodium phosphate buffer (buffer pH 7.36). The mixture was shaken for about 10 seconds at ambient temperature until complete dissolution was obtained. The Falcon tube was allowed to stand at ambient temperature. To this solution, 0.10 g of 8ARM-15K-SG was added. The mixture was shaken to mix for about 10 seconds until all the powder dissolved. 1 mL of the mixture was pipetted out using a mechanical high precision pipette. The gel time of the formulation was collected using the process described above. The gel time was about 1 min 30 seconds.

Example 3: Manufacture of Hydrogel (Thiol-Ester Chemistry

A solution of ETTMP 1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.10 g of 8ARM-15K-SG was added. The mixture was shaken for about 10 seconds until the powder dissolved. 1 mL of the mixture was pipetted out using a mechanical high precision pipette. The gel time was found to be about 3 seconds.

Example 4: Manufacture of Hydrogel (Thiol-Epoxide Chemistry)

A solution of ETTMP 1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.10 g of EJ-190 was added. The mixture was shaken for about 10 seconds until complete dissolution is obtained. 1 mL of the mixture was pipetted out using a mechanical high precision pipette. The gel time was found to be about 6 minutes.

Example 5: Manufacture of Hydrogel Comprising a Therapeutic Agent

In a syringe (Syringe A), about 3 mL of a sodium phosphate buffer (buffer pH 7.36) was measured. About 25 mg of 8ARM-20k-NH2 amine was weighed in a weighing boat and placed as powder in another syringe (Syringe B). About 150 mg of the biodegradable amine 4ARM-20k-AA was weighed in a weighing boat and also placed as a powder in Syringe B. About 4.2 mg cisplatin (or about 45 mg of carboplatin) was weighed in a weighing boat and also placed as a powder in Syringe B. After adding the plunger to Syringe B, the powder contents were mixed. About 75 mg of the ester 8ARM-15k-SG was weighed in a weighing boat and placed as a powder into another syringe (Syringe C).

Syringes A and B containing the buffer and the amine/drug powder, respectively, were connected via a mixing tube. The plunger of the Syringe A (containing the buffer) was pressed until the liquid content was completely transferred to Syringe B (containing the amine/drug). Then the plunger of Syringe B was pressed such that the fluid mixture transfers back to Syringe A. This procedure was repeated until the solids were dissolved. Typically, complete dissolution was achieved in 5 to 10 passes, or approximately 5 to 10 seconds.

The empty syringe was removed from the mixing tube and replaced with Syringe C (containing the ester). Once Syringe C (containing the ester) had been connected to the mixing tube, the timer was started. Immediately, the mixing process was started by pressing the syringe plunger of Syringe B to mix the contents of Syringes C and B. The contents of Syringe C were dissolved in the same fashion as described above. The gel time was measure as described in EXAMPLE 1. The gel time was approximately 90 seconds.

Example 6: In Vitro Bioabsorbance Testing

A 0.10 molar buffer solution of pH 7.40 was prepared with deionized water. A 50 mL portion of this solution was transferred to a Falcon tube. A sample polymer was prepared in a 20 cc syringe. After curing, a 2-4 mm thick slice was cut from the polymer slug and was placed in the Falcon tube. A circulating water bath was prepared and maintained at 37° C. The Falcon tube with polymer was placed inside the water bath and time was started. The dissolution of the polymer was monitored and recorded. The dissolution time ranged from 1-90 days depending on the type of sample polymer.

Example 7: Gelling and Degradation Times

The amine-ester materials explored included: 4ARM-20k-AA/8ARM-20k-NH2 (where x/y is the molar ratio of equivalent functional amine groups of 4ARM-20k-AA to 8ARM-20k-NH2) with an amount of equivalent ester 8ARM-15k-SG present in the sum of x and y; and 4ARM-20k-AA/8ARM-20k-NH2 (50/50) with an alternative ester 4ARM-20k-SGA. Previous results demonstrated the increase in degradation time with a decreasing amount of biodegradable amine (4ARM-20k-AA) and varying the amount of this amine influences the gel and degradation times. The 4ARM-20k-AA/8ARM-20k-NH2 (50/50) formulation was used to load either cisplatin (DDP) or carboplatin (DCP). The alternative ester (4ARM-20k-SGA) was studied in the 4ARM-20k-AA/8ARM-20k-NH2 formulation because it possessed a similar chemical structure to that of the 8ARM-15k-SG ester, but lacks certain hydrolysable moieties that increase the degradation time.

The thiol-ester material explored involved ETTMP-1300, which was the thiol present in either 2/1 or 1/1 molar ratio of equivalent functional groups of thiol to ester. The thiol-ester formulation was evaluated with DDP and DCP to determine whether fundamental polymer properties remained unchanged, since the reactivity of platinum complexes with thiols was well documented in the literature.

Finally, the 4ARM-20k-AA/8ARM-20k-NH2 (50/50) formulation was used to study the effect of mixing time since the polymer formation depends on the dissolution of multiple solids into solution.

Raw Materials & Instrumentation

All reagents were commercially available and used without further purification. The amines and esters (4ARM-20k-AA, 8ARM-20k-NH2, 8ARM-15k-SG, and 4ARM-20k-SGA) were custom synthesized by JenKem Technology and stored under a nitrogen atmosphere. The thiol used (ETTMP-1300) was a trade sample from Chemische Fabrik GmbH&Co., and was stored under a nitrogen atmosphere. DDP and DCP were purchased from Sigma Aldrich and handled in a LabConco Precise HEPA-filtered glove box. For the degradation studies, a Premiere Digital Water Bath Model HH-4 was used to maintain a constant temperature of 36.5° C. The thiol and platinum compounds were weighed to an accuracy of 0.1 mg, while the amines and esters were weighed to an accuracy of 5 mg. A 0.05 M sodium phosphate buffer with a pH between 7.2 and 7.4 was prepared and used for all procedures where indicated. Two 0.05 M sodium borate buffers were prepared with a pH of either 7.94 or 8.35 and used where indicated.

Gel and Degradation Times

The gel time for all experiments was measured starting from the addition of the ester (8ARM-15k-SG or 4ARM-20k-SGA) until the solidification of the solution, which was observed by the absence of fluid motion upon tilting the tube horizontally. Degradation of the polymers was performed by the addition of 5 mL phosphate buffer to 5 g of the material in a 50 mL centrifuge tube and incubating the mixture at 36.5° C. The degradation time was measured starting from the day of addition of the phosphate buffer to complete dissolution of the polymer into solution.

Formulation of Amine-Ester Polymers

The 4ARM-20k-AA and 8ARM-20k-NH2 (typically in the range of 0.1 mmol arms equivalents) was intimately mixed in a 50 mL centrifuge tube. A volume of phosphate buffer was added to the tube via a micropipette such that the final percent of solids in solution was 5 percent. The mixture was shaken briefly before adding the appropriate amount of ester (8ARM-15k-SG). Immediately after adding the ester, the entire solution was shaken for 5 to 10 seconds before letting it rest. 4ARM-20k-AA/8ARM-20k-NH2 molar ratios of 75/25, 60/40, 55/45 and 50/50 were studied (Table 2).

A similar procedure was followed for the formulation of the 4ARM-20k-AA/8ARM-20k-NH2 (50/50) polymer with the alternative ester 4ARM-20k-SGA (Table 3).

TABLE 2

Gel and degradation times for varying 4ARM-20k-AA/8ARM-20k-NH2 ratios with 8ARM-15k-SG ester.

| | 4ARM-20k-AA/8ARM-20k-NH2 | Gel Time (min) | Degradation Time (days) |
|---|---|---|---|
| 1 | 100/0 | 1.30 | 2 to 4 |
| 2 | 75/25 | 1.46 | 5 to 7 |
| 4 | 60/40 | 1.33 | 5 to 7 |
| 5 | 55/45 | 1.33 | 11 to 13 |
| 6 | 50/50 | 1.50 | 15-20 |
| 7 | 0/100 | 1.30 | 56-62 |

TABLE 3

Gel and degradation times for the 4ARM-20k-AA/8ARM-20k-NH2 (50/50) formulation with the new ester (4ARM-20k-SGA).

| 4ARM-20k-AA/8ARM-20k-NH2 | Gel Time (min) | Degradation Time (days) |
|---|---|---|
| 50/50 | 2.50 | >14 |

It was found that decreasing the molar ratio of 4ARM-20k-AA/8ARM-20k-NH2 from 75/25 to 50/50 had no significant effect on gel time, but increased the degradation time from about 6 days to about 15 days. The gel and degradation times of the 4ARM-20k-AA/8ARM-20k-NH2 (50/50) formulation with the alternative ester 4ARM-20k-SGA demonstrated that the degradation time has been prolonged by an as yet undetermined number of days and that the gel time has increased by about one minute.

The data presented in Table 2 demonstrate that the degradation time can be controlled by the 4ARM-20k-AA/8ARM-20k-NH2 ratio.

Formulation of Thiol-Ester Polymers

A volume of borate buffer of a certain pH (pH of 7.94 or 8.35) was added to a 50 mL centrifuge tube via a micropipette such that the final percent of solids in solution was 5 percent. ETTMP-1300 (typically in the range of 0.1 mmol arms equivalents) was dissolved in the buffer with brief shaking. Then, the appropriate amount of ester (8ARM-15k-SG) was added and the entire solution was shaken for 5 to 10 seconds before letting it rest. ETTMP-1300 to 8ARM-15k-SG molar ratios of 2/1 and 1/1 were studied (Table 4).

TABLE 4

Gel time for the ester/thiol (1/1) formulation with two borate buffers of differing pH.

| Borate Buffer ID | pH | Gel Time (min) |
|---|---|---|
| SA-01-17A | 7.94 | 5.00 |
| SA-01-18A | 8.35 | 1.75 |

It was observed that the relatively long gel time of about 5 minutes was significantly decreased to less than 2 minutes by increasing the pH of the borate buffer from 7.94 to 8.35.

The data presented in Table 4 demonstrate that the gel time is controlled by the pH of the buffer. Furthermore, experiments showed that the thiol-ester chemistry required a borate buffer and a higher pH than the amine-ester chemistry, since a phosphate buffer with similar pH did not show any significant polymerization reaction at comparably low pH.

Formulation of Polymers with DDP and DCP

A saturated solution of DDP or DCP in the phosphate and borate buffers was created at 25° C. The final concentration of DDP was 1.3 mg/mL in both the phosphate buffer and borate buffer (pH of 7.94), while the final concentration of DCP was 14.7 mg/mL in the phosphate buffer and 15.6 mg/mL in the borate buffer (pH of 7.94). The amine- and thiol-ester polymers were formulated in the same fashion as previously described, but with the appropriate DDP or DCP buffer solution (Table 5 and Table 6). Samples containing DDP or DCP were protected from light as a precaution.

TABLE 5

Gel and degradation times for the 4ARM-20k-AA/8ARM-20k-NH2 (50/50) formulation with 8ARM-15k-SG ester and DDP or DCP.

| 4ARM-20k-AA/8ARM-20k-NH2 (50/50) | Gel Time (min) | Degradation Time (days) |
|---|---|---|
| DDP | 1.5 | 11 to 14 |
| DCP | 1.5 | >11 |

TABLE 6

Gel and degradation times for the ester/thiol (1/2) formulation with 8ARM-15k-SG ester and DDP or DCP.

| Ester/Thiol (1/2) | Gel Time (min) | Degradation Time (days) |
|---|---|---|
| DDP | 5.33 | >14 |
| DCP | 4.33 | >2 |

The data presented in Table 5 and Table 6 demonstrate that the loading of DDP or DCP into the above formulations appears to have no significant effect on gel and degradation times.

Mixing Time

The mixing time was measured for the 4ARM-20k-AA/8ARM-20k-NH2 (50/50) formulation starting from the addition of the 8-ARM-SG ester and the commencement of shaking the mixture. Gel times were measured for mixing times of 1, 5, 10 and 45 seconds.

TABLE 7

Effect of mixing time on the gel time of the 4ARM-20k-AA/8ARM-20k-NH2 (50/50) formulation with 8ARM-15k-SG ester.

| Mixing Time (s) | Gel Time (min) | |
|---|---|---|
| 1 | 2.33 | |
| 5 | 1.92 | |
| 10 | 1.50 | (2x scale of other data points) |
| 45 | 2.00 | |

The data presented in Table 7 showing the effect of component mixing time on gel time for the 4ARM-20k-AA/8ARM-20k-NH2 (50/50) formulation with 8ARM-15k-SG ester suggests that a sufficient mixing time is between 5 and 10 seconds, and that further mixing has little effect on gel time.

Example 8: Drug Elution from Amine-Ester Hydrogel

Figure 2:
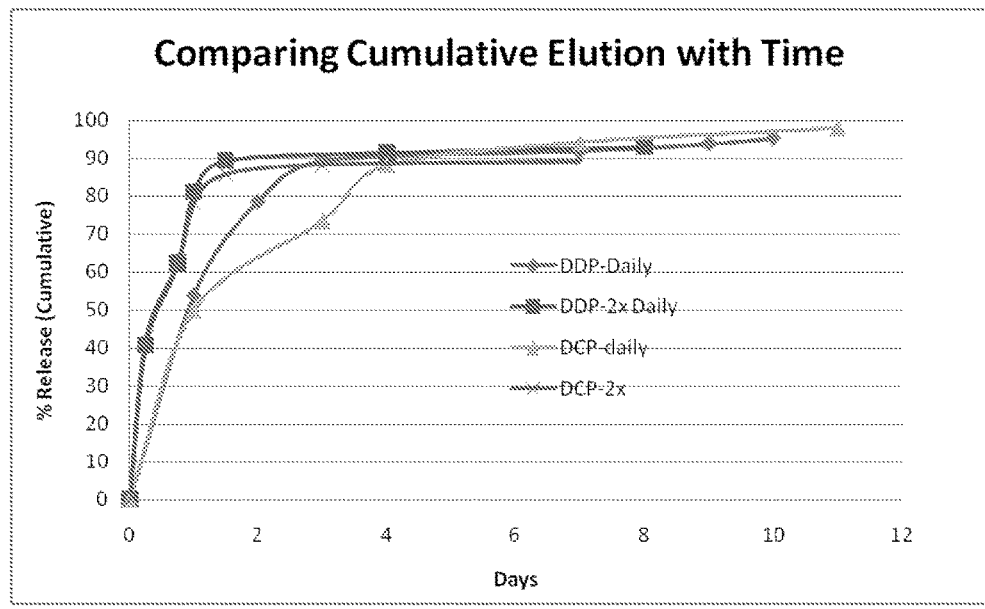
FIG. 2 shows the cumulative elution of carboplatin and cisplatin in PBS buffer using one buffer change per day (daily) or two buffer changes per day (2× daily).

The hydrogel was prepared as described in EXAMPLE 5 using the 4ARM-20k-AA/8ARM-20k-NH2 (50/50) formulation with 8ARM-15k-SG ester and DDP or DCP. Two extraction methods were used: In extraction method 1 one buffer change every 24 hours was performed with 1 mL buffer per gram of polymer; in extraction method 2 two buffer changes were performed per 24 hour period for two days and then one buffer change every 24 hours. The data presented in FIG. 1 and FIG. 2 demonstrate that the in vitro elution kinetics depend on the extraction method, wherein more frequent extraction results in faster elution. Cisplatin and carboplatin have slightly different elution kinetics, but most of the drugs elutes from the polymer with more than 40% of the drugs eluted after one day using either drug.

Example 9: Preparation of Biocompatible Hydrogel Polymer Comprising Docetaxel

The in vivo gelling pharmaceutical pre-formulation forming a biocompatible hydrogel is prepared according to the procedure in EXAMPLE 5, but using docetaxel instead of carboplatin or cisplatin.

Example 10: Preparation of Biocompatible Hydrogel Polymer Comprising Paclitaxel

The in vivo gelling pharmaceutical pre-formulation forming a biocompatible hydrogel is prepared according to the procedure in EXAMPLE 5, but using paclitaxel instead of carboplatin or cisplatin.

Example 11: Preparation of Biocompatible Hydrogel Polymer Comprising Oxaliplatin The in vivo gelling pharmaceutical pre-formulation forming a biocompatible hydrogel is prepared according to the procedure in EXAMPLE 5, but using oxaliplatin instead of carboplatin or cisplatin.

Example 12: Preparation of Biocompatible Hydrogel Polymer Comprising Satraplatin The in vivo gelling pharmaceutical pre-formulation forming a biocompatible hydrogel is prepared according to the procedure in EXAMPLE 5, but using satraplatin instead of carboplatin or cisplatin.

Example 13: Preparation of Biocompatible Hydrogel Polymer Comprising Gemcitabine The in vivo gelling pharmaceutical pre-formulation forming a biocompatible hydrogel is prepared according to the procedure in EXAMPLE 5, but using gemcitabine instead of carboplatin or cisplatin.

Example 14: Preparation of Biocompatible Hydrogel Polymer Comprising Pemetrexed

The in vivo gelling pharmaceutical pre-formulation forming a biocompatible hydrogel is prepared according to the procedure in EXAMPLE 5, but using pemetrexed instead of carboplatin or cisplatin.

Example 15: Preparation of Biocompatible Hydrogel Polymer Comprising Temozolomide The in vivo gelling pharmaceutical pre-formulation forming a biocompatible hydrogel is prepared according to the procedure in EXAMPLE 7: Gelling and Degradation TIMES,
but using temozolomide instead of carboplatin or cisplatin.

Example 16: Preparation of Biocompatible Hydrogel Polymer Comprising Doxorubicin The in vivo gelling pharmaceutical pre-formulation forming a biocompatible hydrogel is prepared according to the procedure in EXAMPLE 5, but using doxorubicin instead of carboplatin or cisplatin.

Example 17: Preparation of Biocompatible Hydrogel Polymer Comprising Diphtheria Toxin The in vivo gelling pharmaceutical pre-formulation forming a biocompatible hydrogel is prepared according to the procedure in EXAMPLE 5, but using diphtheria toxin instead of carboplatin or cisplatin.

Example 18: Preparation of Biocompatible Hydrogel Polymer Comprising α-Hemolysin The in vivo gelling pharmaceutical pre-formulation forming a biocompatible hydrogel is prepared according to the procedure in EXAMPLE 5, but using α-hemolysin instead of carboplatin or cisplatin.

Example 19: Preparation of Biocompatible Hydrogel Polymer Comprising Ciclosporin The in vivo gelling pharmaceutical pre-formulation forming a biocompatible hydrogel is prepared according to the procedure in EXAMPLE 5, but using ciclosporin instead of carboplatin or cisplatin.

Example 20: Preparation of Biocompatible Hydrogel Polymer Comprising Amoxicillin The in vivo gelling pharmaceutical pre-formulation forming a biocompatible hydrogel is prepared according to the procedure in EXAMPLE 5, but using amoxicillin instead of carboplatin or cisplatin.

Example 21: Preparation of Biocompatible Hydrogel Polymer Comprising Methotrexate The in vivo gelling pharmaceutical pre-formulation forming a biocompatible hydrogel is prepared according to the procedure in EXAMPLE 5, but using methotrexate instead of carboplatin or cisplatin.

Example 22: Preparation of Biocompatible Hydrogel Polymer Comprising Etanercept The in vivo gelling pharmaceutical pre-formulation forming a biocompatible hydrogel is prepared according to the procedure in EXAMPLE 5, but using etanercept instead of carboplatin or cisplatin.

Example 23: Preparation of Biocompatible Hydrogel Polymer Comprising Infliximab The in vivo gelling pharmaceutical pre-formulation forming a biocompatible hydrogel is prepared according to the procedure in EXAMPLE 5, but using infliximab instead of carboplatin or cisplatin.

Example 24: Preparation of Biocompatible Hydrogel Polymer Comprising Ibuprofen The in vivo gelling pharmaceutical pre-formulation forming a biocompatible hydrogel is prepared according to the procedure in EXAMPLE 5, but using ibuprofen instead of carboplatin or cisplatin.

Example 25: Preparation of Biocompatible Hydrogel Polymer Comprising Celecoxib The in vivo gelling pharmaceutical pre-formulation forming a biocompatible hydrogel is prepared according to the procedure in EXAMPLE 5, but using celecoxib instead of carboplatin or cisplatin.

Example 26: Preparation of Biocompatible Hydrogel Polymer Comprising Lidocaine The in vivo gelling pharmaceutical pre-formulation forming a biocompatible hydrogel is prepared according to the procedure in EXAMPLE 5, but using lidocaine instead of carboplatin or cisplatin.

Example 27: Delivery of Pre-Formulation into Rabbit Lungs

The goal of the experiment was to test the delivery of a biocompatible hydrogel polymer into the rabbit lung by bronchoscopy. In addition, the safety of the biocompatible hydrogel polymer and the ability of the polymer to stay localized were assessed. Furthermore, changes in histology due to the polymer were evaluated.

Three adult New Zealand rabbits (~5 lbs) and an Olympus bronchoscope BF XP-160F (2.8 mm×600 mm, 1.2 mm working channel) were used in the study. The in vivo gelling pharmaceutical pre-formulation was selected to have an approximately 90 second gel time and a more than 60 days degradation time. The pre-formulation and the saline control comprised about 10% weight/volume barium sulfate for visualization. The rabbits were infused with about 3 mL of pre-formulation or saline solution followed by 7 mL of air.

Two rabbits received the in vivo gelling pharmaceutical pre-formulation, and 1 rabbit received saline as a control. All rabbits survived the entire study period of 15 days. No respiratory difficulty was observed during the study. It was possible to instill solutions in the right middle lobe (RML) in all rabbits without difficulty. The study used approximately 10-times more barium sulfate and 3-times more polymer than what was actually needed. All solutions stayed localized in the RML, including the saline control, mainly because the high concentration of barium sulfate increased the viscosity of the control solution.

In the first rabbit, the pre-formulation was injected rapidly, within about 30-40 seconds. A CT on day 1 showed small right pneumothorax, which was resolved by day 4. The biocompatible hydrogel polymer stayed localized for the entire study. On gross pathology, a thick pleural capsule was observed around the RML. Histology revealed that the polymer distributed into the alveoli although somewhat patchy. Some areas of necrosis and pleura thickening were observed. Upon review, the injection pressure was too high in this study rabbit, causing a bronchopleural fistula (BPF) with pneumothorax and patchy distribution of the polymer. The polymer appeared to have sealed the BPF and the pneumothorax resolved within 4 days, allowing the rabbit to survive for the whole 15 day study period.

For the second rabbit, there was some difficulty with getting the polymer ready for injection, which resulted in a delay in polymer injection as compared to the first rabbit. Some polymer actually gelled on the tip of the bronchoscope, but was easily wiped off with gauze. Some polymer was seen stuck onto the tracheal wall, probably after being brushed on as the bronchoscope was pulled out. Efforts to suction the polymer off the tracheal wall were unsuccessful, as the polymer appeared to adhere fairly well to the tissue. Gross pathology showed an even distribution of the polymer in the alveoli. Histology showed a preserved lung architecture and no necrosis. Furthermore, giant cells and granulomas had formed, but no fibrosis or necrosis was observed and the pleura was intact with slightly thickened alveolar membrane but no destruction of the capillaries. These observations show that the polymer should be administered using a low injection pressure.

In the rabbit given the saline control solution, the addition of barium sulfate created a somewhat thick, final solution at baseline with an increased viscosity due to the barium sulfate. After instillation, some barium sulfate/saline solution was seen welling out of the RML bronchus, which was not observed for the rabbits administered with the pre-formulation. On gross pathology, the RML was much smaller. On histology, primarily foamy macrophages and no granulomas were observed. The barium sulfate was deposited in the alveoli and was localized in the RML.

In conclusion, the pre-formulation was easy to deliver and stayed localized. It appeared to be safe, entered the alveoli and could not be coughed out. The rabbits survived large volumes of hydrogel polymer in their lungs without difficulty (3 mL of hydrogel polymer in a rabbit lung is approximately equivalent to about 180 mL in a human lung). The changes in histology due to the polymer were minor and not life threatening or serious and are expected to disappear once the polymer degrades.

Example 28: Verification of Curing Post-Administration

The hydrogel is prepared in a mixing vessel as described above. A desired amount of hydrogel is removed from the mixing vessel for delivery to the target site. Appropriate curing of the biocompatible hydrogel polymer at the target site is verified by evaluating the residual hydrogel left in the mixing vessel. A lack of flow indicates that the hydrogel is cured.

Example 29: Delivery of Hydrogel to Lung Tumor Through Bronchoscope

A rabbit model of lung cancer is created by subculturing VX2 cells derived from rabbit skin squamous cell carcinoma in the femoral muscle of a rabbit. VX2 tumors are excised, washed, and suspended in collagen gel matrix. $1 \times 10^8$ VX2 tumor cells are instilled into the right middle lobe (RML) and left lower lobes (LLL) of the rabbit lung under sedation using a pediatric bronchoscope with an outer diameter of 3.6 mm and working channel of 1.2 mm. Rabbits are imaged every 1 week using an animal CT scanner until tumor formation is detected. An in vivo gelling pharmaceutical pre-formulation comprising a chemotherapeutic anticancer agent (e.g., cisplatin) is delivered to the RML tumor only using a pediatric bronchoscope with 1.2 mm outer diameter catheter inserted through the working channel to deliver the pre-formulation. Tumor size is measured by CT imaging every 5-7 days. Tumor volume is measured by semi-automatic segmentation using active contour methods with the program ITK-SNAP. Tumor size of the treated RML tumor is directly compared to the tumor size of the untreated LLL tumor in the same animal. Rabbits are closely monitored for any side effects from biocompatible hydrogel polymer delivery. At the end of the study, rabbits are euthanized and necropsies are performed for detailed histological and pathologic analysis of the lung and lung cancers.

Example 30: Elution Kinetic of Drugs in Rabbit Model

Rabbits with specific doses of a biocompatible hydrogel polymer delivered into the lung by bronchoscopy have blood drawn at time intervals 30 min, 1 hour, 2 hours, 3 hours, 6 hours, 12 hours, 24 hours, 48 hours, 5 days, 10 days, 20 days, and 30 days for measurement of therapeutic agent drug levels in the serum. These blood draws are performed in different rabbits at different therapeutic agent doses to generate drug absorption and drug elution curves for the biocompatible hydrogel polymer. Serum drug levels are measured by high-performance liquid chromatography (HPLC) or other quantitative methods.

Example 31: Clinical Trial for the Treatment of Lung Cancer

The study goal is to evaluate the safety and efficacy of an in vivo gelling pharmaceutical pre-formulation forming a biocompatible hydrogel polymer containing cisplatin and/or carboplatin in the treatment of primary lung malignancies and pulmonary metastases. The study endpoints are local tumor control and lack of adverse events.

The inclusion criteria for admittance to the study are patients with one or more primary or secondary lung malignancies who are not candidates for or reject surgical resection, having a Karnofsky Index of >70%, and are not requiring home oxygen. The patient population for the study is 30 male and female patients.

Prior to treatment, CT thorax is obtained within 2 weeks of the procedure and the tumor is identified. Bronchoscopy is performed in the outpatient setting under conscious sedation with IV fentanyl and midazolam in incremental doses. The bronchoscope is navigated to the area of the tumor identified on CT with either visual guidance only or visual guidance plus electromagnetic navigational guidance (at the discretion of the operator). The cisplatin or carboplatin pre-formulation (30 mL) is instilled in the appropriate area of the lung through a catheter inserted through the working channel of the bronchoscope over 45-60 seconds. Blood is drawn within 2 hours after the procedure to measure serum cisplatin or carboplatin levels, chemistry panel, and blood count. The patient is discharged home after the procedure.

Follow-up clinical examination is performed at day 1, day 7, day 30, and every 12 weeks after the procedure for an intended follow-up period of 2 years. Each clinical visit is accompanied by blood sampling. CT thorax is performed at day 30, week 12, and every 6 months for total of 2 years.

Remission criteria and local control rates after treatment with the biodegradable hydrogel polymer are defined according to modified WHO response criteria for solid tumors and represents either stable disease (SD), partial (PR) or complete remission (CR) of the treated lesion. Any increase >20% in diameter of a singular lesion is interpreted as progression.

Example 32: Clinical Trial for the Treatment of Mesothelioma

The study goal is to evaluate the safety and efficacy of a intrapleurally infused in vivo gelling pharmaceutical pre-formulation forming a biocompatible hydrogel polymer containing cytotoxin or a chemotherapeutic anticancer agent in patients with malignant pleural mesothelioma (MPM) localized to one hemithorax. The study endpoints are local tumor control and lack of adverse events.

The inclusion criteria for admittance to the study are patients with histologically confirmed MPM who are not candidates for or reject other treatment options (chemotherapy, extrapleural pneumonectomy, radiation therapy), having a Karnofsky Index of >60% and for whom preventive radiotherapy of the point of entry of the thoracoscope is recommended. The patient population for the study is 15 male and female patients.

Prior to treatment, CT thorax is obtained within 2 weeks of the procedure and the extent of MPM identified. Thoracoscopy is performed in the operating room under general anesthesia and any effusion is drained. An in vivo gelling pharmaceutical pre-formulation comprising cytotoxin or an anticancer agent (50 to 100 mL) are sprayed onto the areas of MPM identified by thoracoscopy. Blood is drawn within 2 hours after the procedure to measure serum anticancer agent or cytotoxin levels, chemistry panel, and blood count. The patient is hospitalized for at least 3 days after the procedure to ensure complete recovery.

Follow-up clinical examination is performed at day 1, day 3, day 14, and every 8 weeks after the procedure for an intended follow-up period of 1 year. Each clinical visit is accompanied by blood sampling. CT thorax is performed at day 14, week 8, and every 3-4 months for a total of 1 year.

Remission criteria and local control rates after treatment are defined according to modified RECIST criteria for MPM based on tumor thickness perpendicular to the chest wall or mediastinum. Patients are characterized as having stable disease (SD), partial remission (PR), or complete remission (CR). Any increase >20% in total tumor measurement or appearance of new lesions is interpreted as progression.

Example 33: Clinical Trial for the Treatment of Bronchopleural Fistula

Patients with a post-pneumonectomy or post-lobectomy bronchopleural fistula (BPF) are treated by bronchoscopic injection of an in vivo gelling pharmaceutical pre-formulation forming a biocompatible hydrogel polymer. The patients are also treated with a chest drain. All patients have undergone lung resection for cancer and present an early fistula. The bronchial stump has been closed by a mechanical stapler or sutures in all patients.

According to the modified classification of Le Brigand, fistulas are considered early if occurring within 1-7 days after lung resection. The occurrence of fistula is from 3 to 7 days after the operation (mean: 5.6 days). The diameter of the fistula is between 3-10 mm. All patients are examined by computed tomography (CT) of the chest and bronchoscopy. In all patients, a chest drain is inserted at the time of fistula diagnosis.

Endoscopic treatment consists of repeated (once every 48 h for a maximum of five applications) injections of the in vivo gelling pharmaceutical pre-formulation forming a biocompatible polymer on the margins of the fistula. All procedures are performed using a flexible bronchoscope with an operative channel. When the in vivo gelling pharmaceutical pre-formulation is ready, an endoscopic catheter is advanced through the operative channel of the flexible bronchoscope and several deliveries of the pre-formulation are performed at the margins of the fistula under direct vision. A maximum of five endoscopic applications for each patient is planned. In case of persistent fistula after the fifth application, surgical repair would subsequently be planned.

The chest drain is removed after the disappearance of air leaks if bronchoscopy shows a complete resolution of the fistula.

Example 34: Clinical Trial for the Treatment of Rheumatoid Arthritis

This is a single-center, placebo controlled phase I/IIa clinical trial of a biocompatible hydrogel polymer comprising a therapeutic study agent.

Patients enter the study following the diagnosis of rheumatoid arthritis (RA) based on ACR (American college of Rheumatology) criteria, if they meet the following inclusion/exclusion criteria. Inclusion criteria are: (a) no significant improvement in clinical condition after treatment with disease-modifying anti-rheumatic drugs (DMARDs) for more than 3 months, (b) age between 35 and 65 years, and (c) presence of Steinbrocker stage I and II synovitis on radiographs of the knee joints. Exclusion criteria are: (a) previous surgical procedure on the studied knee, (b) intra- or periarticular infection, (c) hepatic or renal dysfunction, (d) bleeding tendency with prothrombin time below 50% of normal value and difficult to correct by blood transfusion or other measures, and (e) pregnant or breast-feeding women.

To increase the patients' compliance, concomitant administration of previous medication for RA, including non-steroidal anti-inflammatory drugs (NSAIDs), DMARDs, and prednisolone (maximal dose of 10 mg/day), is allowed during the study on the condition that the dosage and administration of the medication would not be altered during the period from 2 weeks preceding the study until the end of the study.

Each patient undergoes a complete clinical and laboratory evaluation before entry into the study, including medical history, physical examination and laboratory examinations [complete blood count, urinalysis, erythrocyte sedimentation rate, C-reactive protein, serum electrolytes, blood urea nitrogen (BUN), creatinine, aspartate aminotransferase (AST), alanine aminotransferase (ALT), total bilirubin, alkaline phosphatase, lactate dehydrogenase (LDH), prothrombin time, serum albumin and serum total protein]. Antero-posterior and lateral radiographs of involved knee joint are obtained before the injection and the knees are classified according to Steinbrocker staging criteria of RA.

The study subjects are randomly allocated to treatment with the biocompatible hydrogel polymer only or treatment with the biocompatible hydrogel polymer comprising a therapeutic study drug. Pharmacokinetic parameters are evaluated in three patients of each group, which included area under the curve (AUC) for plasma concentration of study drug and maximum plasma concentration.

With the patient supine, the site for the injection is washed with an iodine solution and 1% lidocaine solution is injected for local anesthesia of the skin and subcutaneous tissues of the injection area. A standard medial or lateral parapatellar approach is used. Two mL of synovial fluid is withdrawn using a syringe with a 21-gauge needle, followed by the injection of 1 ml of the in vivo gelling pre-formulation comprising the study drug (e.g., methotrexate) and cleansing by flushing with 1 ml of 1% lidocaine solution. The knee effusion is not drained to completion prior to injection of the biocompatible hydrogel polymer so that the circumference of the knee joint could be maintained before and after injection. Thereafter, the knee is immobilized for 6 h by bed rest in full extension. Patients are advised to rest without bearing excessive weight on the knee joints for at least 3 days after the injection. Follow-up evaluations of patients are performed 1 and 4 days, and 1, 2, 4, 8 and 12 weeks after the injection. At baseline and follow-up studies, the following items are evaluated in each patient: subjective symptoms, vital signs (pulse rate, blood pressure and body temperature), electrocardiogram, physical examination and laboratory examinations, including hematological examination, blood chemistry, urinalysis, and in less frequent intervals the fate of the in vivo polymerized biocompatible hydrogel polymer.

At baseline and follow-up clinical examinations (1, 4, 8 and 12 weeks after the injection), the following parameters are evaluated: knee joint pain, range of motion and knee joint swelling. Knee joint pain is measured using the 100-mm horizontal visual analogue scale (VAS) (0, no pain; 100, most severe pain), range of motion by measuring the flexion range using a goniometer, and swelling by measuring the knee circumference around the centre of the patella. Based on these measurements, the patient's response to treatment is assessed clinically as good, fair or poor at 12 weeks after the procedure. Patients with a good response have almost complete relief of pain, a diminished joint effusion and improved range of motion. Patients with a fair response have partial relief of pain, a diminished effusion and maintenance of the preoperative range of motion. Patients with a poor response have no benefit from the treatment, with continued pain, effusion or aggravation of limited range of motion.

What is claimed is:

1. An in vivo gelling pharmaceutical pre-formulation, comprising:
    (a) at least one multifunctional nucleophilic monomer comprising a polyol core, wherein the polyol core is selected from the group consisting of:

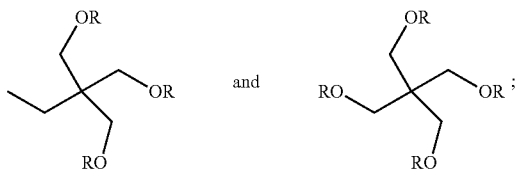

and
    wherein R is:

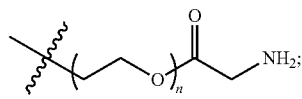

wherein n is 10-200 and the molecular weight of the nucleophilic monomer is between about 2,000 to about 40,000;

(b) at least one water soluble second compound comprising more than one electrophilic group selected from an epoxide, N-succinimidyl succinate, N-succinimidyl glutarate, N-succinimidyl succinamide or N-succinimidyl glutaramide, wherein the second compound comprising the core of one electrophilic group is a pentaerythritol, and wherein the second compound further comprises one or more polyethylene glycol sections; and
    (c) an aqueous buffer in the pH range of 5.0 to 9.0;
wherein mixing a mixture comprising the at least one multifunctional nucleophilic monomer and the at least one water soluble second compound in the aqueous buffer and delivering the mixture to a target site in the human body generates the in vivo gelling pharmaceutical pre-formulation such that the in vivo gelling pharmaceutical pre-formulation at least in part polymerizes and gels at the target site to form a biocompatible hydrogel polymer, and wherein the in vivo gelling pharmaceutical pre-formulation does not contain blood or protein.

2. The in vivo gelling pharmaceutical pre-formulation of claim 1, wherein the molecular weight of each of the second compound is independently between about 500 and 40000.

3. The in vivo gelling pharmaceutical pre-formulation of claim 1, wherein the second compound is selected from the group consisting of ethoxylated pentaerythritol succinimidyl succinate, ethoxylated pentaerythritol succinimidyl glutarate, and ethoxylated pentaerythritol succinimidyl glutaramide.

4. The in vivo gelling pharmaceutical pre-formulation of claim 1, further comprising a therapeutic agent selected from the group consisting of an anticancer agent, an antiviral agent, an antibacterial agent, antifungal agent, an immunosuppressant agent, an hemostasis agent, and an anti-inflammatory agent.

5. The in vivo gelling pharmaceutical pre-formulation of claim 1, wherein the pH of the aqueous buffer is from about 6.9 to about 7.9.

6. The in vivo gelling pharmaceutical pre-formulation of claim 1, wherein the biocompatible hydrogel polymer is bioabsorbed within about 1 to 70 days.

7. The in vivo gelling pharmaceutical pre-formulation of claim 1, wherein the biocompatible hydrogel polymer is substantially non-bioabsorbable.

8. The biocompatible hydrogel polymer of claim 1.

9. The in vivo gelling pharmaceutical pre-formulation of claim 1, further comprising a second multifunctional nucleophilic monomer comprising more than one nucleophilic group, wherein the second multifunctional nucleophilic monomer is a polyol substituted with R', wherein R' is:

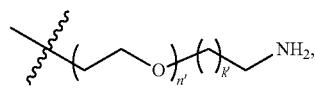

wherein n' is 1-200, and
wherein k' is 1-6.

10. The in vivo gelling pharmaceutical pre-formulation of claim 1, wherein the polyol core of the multifunctional nucleophilic monomer is:

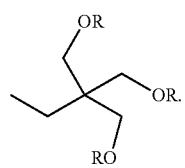

11. The in vivo gelling pharmaceutical pre-formulation of claim 1, wherein the polyol core of the multifunctional nucleophilic monomer is:

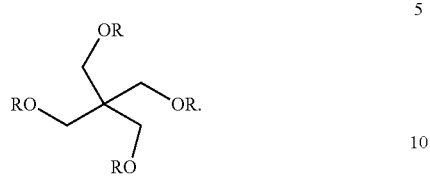

12. The in vivo gelling pharmaceutical pre-formulation of claim 1, wherein the in vivo gelling pharmaceutical pre-formulation does not contain biological materials.

13. The in vivo gelling pharmaceutical pre-formulation of claim 1, wherein the molecular weight of the multifunctional nucleophilic monomer is between about 5,000 to about 20,000.

14. The in vivo gelling pharmaceutical pre-formulation of claim 1, wherein the mixture comprising at least one multifunctional nucleophilic monomer and the at least one water soluble second compound comprising more than one electrophilic group comprising 4ARM-20k-AA and 4ARM-20k-SGA.

* * * * *